(12) United States Patent
Hoey et al.

(10) Patent No.: US 11,992,254 B2
(45) Date of Patent: *May 28, 2024

(54) MEDICAL DEVICES AND METHODS

(71) Applicant: Boston Scientific Scimed, Inc., Maple Grove, MN (US)

(72) Inventors: Michael Hoey, Shoreview, MN (US); Roger Noel Hastings, Naples, FL (US); Mark Schrom, Forest Lake, MN (US); Matthew Byrne, Minneapolis, MN (US); Grant Mauch, Delano, MN (US); Eric Jerke, Bloomington, MN (US); Richard Charles Kravik, Champlin, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 482 days.

This patent is subject to a terminal disclaimer.

(21) Appl. No.: 16/919,499

(22) Filed: Jul. 2, 2020

(65) Prior Publication Data
US 2020/0397495 A1    Dec. 24, 2020

Related U.S. Application Data

(63) Continuation of application No. 15/864,957, filed on Jan. 8, 2018, now Pat. No. 10,751,107.
(Continued)

(51) Int. Cl.
*A61B 18/04*    (2006.01)
*A61B 18/08*    (2006.01)
(Continued)

(52) U.S. Cl.
CPC ............ *A61B 18/082* (2013.01); *A61B 18/04* (2013.01); *A61B 18/10* (2013.01); *A61B 90/04* (2016.02);
(Continued)

(58) Field of Classification Search
CPC ....... A61B 18/04; A61B 18/082; A61B 18/10; A61B 2018/00023; A61B 2018/00029;
(Continued)

(56) References Cited

U.S. PATENT DOCUMENTS

| 408,899 A | 8/1889 | Small |
| 1,719,750 A | 7/1929 | Bridge et al. |

(Continued)

FOREIGN PATENT DOCUMENTS

| CN | 2061443 U | 9/1990 |
| CN | 2418844 Y | 2/2001 |

(Continued)

OTHER PUBLICATIONS

US 5,326,343 A, 07/1994, Rudie et al. (withdrawn)
(Continued)

*Primary Examiner* — Michael F Peffley
(74) *Attorney, Agent, or Firm* — Bookoff McAndrews, PLLC

(57) ABSTRACT

A vapor delivery needle is provided that may include any of a number of features. One feature of the energy delivery probe is that it can apply condensable vapor energy to tissue, such as a prostrate, to shrink, damage, or denature tissues of the prostate. Methods associated with use of the energy delivery probe are also covered.

17 Claims, 17 Drawing Sheets

Related U.S. Application Data

(60) Provisional application No. 62/443,555, filed on Jan. 6, 2017.

(51) Int. Cl.
 *A61B 18/10* (2006.01)
 *A61B 90/00* (2016.01)
 *A61B 18/00* (2006.01)

(52) U.S. Cl.
 CPC ........... *A61B 2018/00023* (2013.01); *A61B 2018/00029* (2013.01); *A61B 2018/00047* (2013.01); *A61B 2018/00083* (2013.01); *A61B 2018/00101* (2013.01); *A61B 2018/00285* (2013.01); *A61B 2018/00547* (2013.01); *A61B 2018/00577* (2013.01); *A61B 2018/00821* (2013.01); *A61B 2018/00869* (2013.01); *A61B 2018/00875* (2013.01); *A61B 2018/00898* (2013.01); *A61B 2018/00982* (2013.01); *A61B 2018/048* (2013.01); *A61B 2090/0427* (2016.02); *A61B 2090/0436* (2016.02)

(58) Field of Classification Search
 CPC ........... A61B 2018/00047; A61B 2018/00083; A61B 2018/00101; A61B 2018/00285; A61B 2018/00547; A61B 2018/00577; A61B 2018/00821; A61B 2018/00869; A61B 2018/00875; A61B 2018/00898; A61B 2018/00982; A61B 2018/048; A61B 2090/0427; A61B 2090/0436
 See application file for complete search history.

(56) References Cited

U.S. PATENT DOCUMENTS

| | | |
|---|---|---|
| 4,672,963 A | 6/1987 | Barken |
| 4,920,982 A | 5/1990 | Goldstein |
| 4,950,267 A | 8/1990 | Ishihara et al. |
| 5,117,482 A | 5/1992 | Hauber |
| 5,222,185 A | 6/1993 | McCord, Jr. |
| 5,249,585 A | 10/1993 | Turner et al. |
| 5,300,099 A | 4/1994 | Rudie |
| 5,312,399 A | 5/1994 | Hakky et al. |
| 5,330,518 A | 7/1994 | Neilson et al. |
| 5,341,807 A * | 8/1994 | Nardella ............ A61B 18/1492 606/41 |
| 5,366,490 A | 11/1994 | Edwards et al. |
| 5,370,609 A | 12/1994 | Drasler et al. |
| 5,370,675 A | 12/1994 | Edwards et al. |
| 5,370,677 A | 12/1994 | Rudie et al. |
| 5,385,544 A | 1/1995 | Edwards et al. |
| 5,409,453 A | 4/1995 | Lundquist et al. |
| 5,413,588 A | 5/1995 | Rudie et al. |
| 5,421,819 A | 6/1995 | Edwards et al. |
| 5,435,805 A | 7/1995 | Edwards et al. |
| 5,464,437 A | 11/1995 | Reid et al. |
| 5,470,308 A | 11/1995 | Edwards et al. |
| 5,470,309 A | 11/1995 | Edwards et al. |
| 5,484,400 A | 1/1996 | Edwards et al. |
| 5,499,998 A | 3/1996 | Meade |
| 5,531,676 A | 7/1996 | Edwards et al. |
| 5,531,763 A | 7/1996 | Mastri et al. |
| 5,542,915 A | 8/1996 | Edwards et al. |
| 5,542,916 A | 8/1996 | Hirsch et al. |
| 5,545,171 A | 8/1996 | Sharkey et al. |
| 5,549,644 A | 8/1996 | Lundquist et al. |
| 5,554,110 A | 9/1996 | Edwards et al. |
| 5,556,377 A | 9/1996 | Rosen et al. |
| 5,558,673 A | 9/1996 | Edwards et al. |
| 5,588,960 A | 12/1996 | Edwards et al. |
| 5,591,125 A | 1/1997 | Edwards et al. |
| 5,599,294 A | 2/1997 | Edwards et al. |
| 5,601,591 A | 2/1997 | Edwards et al. |
| 5,628,770 A | 5/1997 | Thorne et al. |
| 5,630,794 A | 5/1997 | Lax et al. |
| 5,645,528 A | 7/1997 | Thorne |
| 5,667,488 A | 9/1997 | Lundquist et al. |
| 5,672,153 A | 9/1997 | Lax et al. |
| 5,709,680 A | 1/1998 | Yates et al. |
| 5,720,718 A | 2/1998 | Rosen et al. |
| 5,720,719 A | 2/1998 | Edwards et al. |
| 5,776,176 A | 7/1998 | Rudie |
| 5,792,070 A | 8/1998 | Kauphusman et al. |
| 5,797,903 A | 8/1998 | Swanson et al. |
| 5,800,486 A | 9/1998 | Thorne et al. |
| 5,807,395 A | 9/1998 | Mulier et al. |
| 5,830,179 A | 11/1998 | Mikus et al. |
| 5,843,144 A | 12/1998 | Rudie et al. |
| 5,849,011 A | 12/1998 | Jones et al. |
| 5,861,021 A | 1/1999 | Thorne et al. |
| 5,871,481 A | 2/1999 | Kannenberg et al. |
| 5,873,877 A | 2/1999 | McGaffigan et al. |
| 5,897,553 A | 4/1999 | Mulier et al. |
| 5,899,932 A | 5/1999 | Dann et al. |
| 5,938,692 A | 8/1999 | Rudie |
| 5,944,715 A | 8/1999 | Goble et al. |
| 5,951,515 A | 9/1999 | Osterlind |
| 5,957,922 A | 9/1999 | Imran |
| 5,964,752 A | 10/1999 | Stone |
| 5,964,756 A | 10/1999 | McGaffigan et al. |
| 5,976,123 A | 11/1999 | Baumgardner et al. |
| 5,987,360 A | 11/1999 | McGrath et al. |
| 5,990,465 A | 11/1999 | Nakaoka et al. |
| 6,007,571 A | 12/1999 | Neilson et al. |
| 6,009,351 A | 12/1999 | Flachman |
| 6,017,358 A | 1/2000 | Yoon et al. |
| 6,017,361 A | 1/2000 | Mikus et al. |
| 6,036,631 A | 3/2000 | McGrath et al. |
| 6,036,713 A | 3/2000 | Kieturakis |
| 6,053,909 A | 4/2000 | Shadduck |
| 6,063,081 A | 5/2000 | Mulier et al. |
| 6,067,475 A | 5/2000 | Graves et al. |
| 6,077,257 A | 6/2000 | Edwards et al. |
| 6,113,593 A | 9/2000 | Tu et al. |
| 6,122,551 A | 9/2000 | Rudie et al. |
| 6,123,083 A | 9/2000 | McGrath et al. |
| 6,147,336 A | 11/2000 | Oshijima et al. |
| 6,148,236 A | 11/2000 | Dann |
| 6,156,036 A | 12/2000 | Sussman et al. |
| 6,161,049 A | 12/2000 | Rudie et al. |
| 6,179,805 B1 | 1/2001 | Sussman et al. |
| 6,179,836 B1 | 1/2001 | Eggers et al. |
| 6,206,847 B1 | 3/2001 | Edwards et al. |
| 6,210,404 B1 | 4/2001 | Shadduck |
| 6,210,406 B1 * | 4/2001 | Webster ............ A61B 18/1492 606/41 |
| 6,223,085 B1 | 4/2001 | Dann et al. |
| 6,231,591 B1 | 5/2001 | Desai |
| 6,238,389 B1 | 5/2001 | Paddock et al. |
| 6,238,391 B1 | 5/2001 | Olsen et al. |
| 6,238,393 B1 | 5/2001 | Mulier et al. |
| 6,241,702 B1 | 6/2001 | Lundquist et al. |
| 6,258,087 B1 | 7/2001 | Edwards et al. |
| 6,272,384 B1 | 8/2001 | Simon et al. |
| 6,287,297 B1 | 9/2001 | Woodruff et al. |
| 6,302,903 B1 | 10/2001 | Mulier et al. |
| 6,312,391 B1 | 11/2001 | Ramadhyani et al. |
| 6,315,777 B1 | 11/2001 | Comben |
| 6,348,039 B1 | 2/2002 | Flachman et al. |
| 6,398,759 B1 | 6/2002 | Sussman et al. |
| 6,409,722 B1 | 6/2002 | Hoey et al. |
| 6,423,027 B1 | 7/2002 | Gonon |
| 6,440,127 B2 | 8/2002 | McGovern et al. |
| 6,461,296 B1 | 10/2002 | Desai |
| 6,494,902 B2 | 12/2002 | Hoey et al. |
| 6,496,737 B2 | 12/2002 | Rudie et al. |
| 6,508,816 B2 | 1/2003 | Shadduck |
| 6,517,534 B1 | 2/2003 | McGovern et al. |
| 6,524,270 B1 | 2/2003 | Bolmsjo et al. |
| 6,537,248 B2 | 3/2003 | Mulier et al. |
| 6,537,272 B2 | 3/2003 | Christopherson et al. |
| 6,544,211 B1 | 4/2003 | Andrew et al. |

(56) References Cited

U.S. PATENT DOCUMENTS

| | | |
|---|---|---|
| 6,551,300 B1 | 4/2003 | McGaffigan |
| 6,565,561 B1 | 5/2003 | Goble et al. |
| 6,575,929 B2 | 6/2003 | Sussman et al. |
| 6,575,968 B1 | 6/2003 | Eggers et al. |
| 6,579,270 B2 | 6/2003 | Sussman et al. |
| 6,589,201 B1 | 7/2003 | Sussman et al. |
| 6,607,529 B1 | 8/2003 | Jones et al. |
| 6,638,275 B1 | 10/2003 | McGaffigan et al. |
| 6,640,139 B1 | 10/2003 | Ueberle |
| 6,669,694 B2 | 12/2003 | Shadduck |
| 6,676,628 B2 | 1/2004 | Sussman et al. |
| 6,706,039 B2 | 3/2004 | Mulier et al. |
| 6,716,252 B2 | 4/2004 | Lazarovitz et al. |
| 6,719,738 B2 | 4/2004 | Mehier |
| 6,726,696 B1 | 4/2004 | Houser et al. |
| 6,730,079 B2 | 5/2004 | Lovewell |
| 6,736,810 B2 | 5/2004 | Hoey et al. |
| 6,740,108 B1 | 5/2004 | Just et al. |
| 6,760,616 B2 * | 7/2004 | Hoey .......... A61B 5/0538 600/554 |
| 6,780,178 B2 | 8/2004 | Palanker et al. |
| 6,827,718 B2 | 12/2004 | Hutchins et al. |
| 6,855,141 B2 | 2/2005 | Lovewell |
| 6,887,237 B2 | 5/2005 | McGaffigan |
| 6,905,475 B2 | 6/2005 | Hauschild et al. |
| 6,911,028 B2 | 6/2005 | Shadduck |
| 6,969,376 B2 | 11/2005 | Takagi et al. |
| 6,974,455 B2 | 12/2005 | Garabedian et al. |
| 7,014,652 B2 | 3/2006 | Cioanta et al. |
| 7,041,121 B1 | 5/2006 | Williams et al. |
| 7,066,935 B2 | 6/2006 | Swoyer et al. |
| 7,089,064 B2 | 8/2006 | Manker et al. |
| 7,130,697 B2 | 10/2006 | Chomenky et al. |
| 7,238,182 B2 | 7/2007 | Swoyer et al. |
| 7,247,155 B2 | 7/2007 | Hoey et al. |
| 7,261,709 B2 | 8/2007 | Swoyer et al. |
| 7,261,710 B2 | 8/2007 | Elmouelhi et al. |
| 7,322,974 B2 | 1/2008 | Swoyer et al. |
| 7,328,068 B2 | 2/2008 | Spinelli et al. |
| 7,328,069 B2 | 2/2008 | Gerber |
| 7,335,197 B2 | 2/2008 | Sage et al. |
| 7,340,300 B2 | 3/2008 | Christopherson et al. |
| 7,369,894 B2 | 5/2008 | Gerber |
| 7,429,262 B2 | 9/2008 | Woloszko et al. |
| 7,437,194 B2 | 10/2008 | Skwarek et al. |
| 7,470,228 B2 | 12/2008 | Connors et al. |
| 7,549,987 B2 | 6/2009 | Shadduck |
| 7,865,250 B2 | 1/2011 | Mrva et al. |
| 7,894,913 B2 | 2/2011 | Boggs et al. |
| 7,959,577 B2 | 6/2011 | Schmitz et al. |
| 8,016,823 B2 | 9/2011 | Shadduck |
| 8,048,069 B2 | 11/2011 | Skwarek et al. |
| 8,216,217 B2 | 7/2012 | Sharkey et al. |
| 8,244,327 B2 | 8/2012 | Fichtinger et al. |
| 8,251,985 B2 | 8/2012 | Hoey et al. |
| 8,272,383 B2 | 9/2012 | Hoey et al. |
| 8,273,079 B2 | 9/2012 | Hoey et al. |
| 8,301,264 B2 | 10/2012 | Achenbach et al. |
| 8,313,485 B2 | 11/2012 | Shadduck |
| 8,372,065 B2 | 2/2013 | Hoey et al. |
| 8,388,611 B2 | 3/2013 | Shadduck et al. |
| 8,409,109 B2 | 4/2013 | Tiesma et al. |
| 8,419,723 B2 | 4/2013 | Shadduck et al. |
| 8,470,957 B2 | 6/2013 | Hikosaka et al. |
| 8,550,743 B2 | 10/2013 | Bonde et al. |
| 8,585,692 B2 | 11/2013 | Shadduck et al. |
| 8,632,530 B2 | 1/2014 | Hoey et al. |
| 8,721,632 B2 * | 5/2014 | Hoey .......... A61B 18/18 604/113 |
| 8,801,702 B2 | 8/2014 | Hoey et al. |
| 8,900,223 B2 | 12/2014 | Shadduck |
| 9,198,708 B2 | 12/2015 | Hoey et al. |
| 9,204,922 B2 * | 12/2015 | Hooven .......... A61B 18/1492 |
| 9,345,507 B2 | 5/2016 | Hoey et al. |
| 9,526,555 B2 | 12/2016 | Hoey et al. |
| 9,833,277 B2 | 12/2017 | Hoey et al. |
| 9,895,185 B2 | 2/2018 | Hoey et al. |
| 2002/0078956 A1 | 6/2002 | Sharpe et al. |
| 2002/0111617 A1 | 8/2002 | Cosman et al. |
| 2002/0177846 A1 | 11/2002 | Mulier et al. |
| 2003/0069575 A1 | 4/2003 | Chin et al. |
| 2003/0092689 A1 | 5/2003 | Escandon et al. |
| 2003/0097126 A1 | 5/2003 | Woloszko et al. |
| 2003/0130575 A1 | 7/2003 | Desai |
| 2003/0206730 A1 | 11/2003 | Golan |
| 2004/0006334 A1 | 1/2004 | Beyar et al. |
| 2004/0068306 A1 | 4/2004 | Shadduck |
| 2004/0186422 A1 | 9/2004 | Rioux et al. |
| 2004/0230316 A1 | 11/2004 | Cioanta et al. |
| 2004/0267340 A1 | 12/2004 | Cioanta et al. |
| 2005/0096629 A1 | 5/2005 | Gerber et al. |
| 2005/0124915 A1 | 6/2005 | Eggers et al. |
| 2005/0149020 A1 | 7/2005 | Jahng |
| 2005/0159676 A1 | 7/2005 | Taylor et al. |
| 2005/0159678 A1 | 7/2005 | Taylor et al. |
| 2006/0089636 A1 | 4/2006 | Christopherson et al. |
| 2006/0135955 A1 | 6/2006 | Shadduck |
| 2006/0178670 A1 | 8/2006 | Woloszko et al. |
| 2006/0224154 A1 | 10/2006 | Shadduck et al. |
| 2006/0224169 A1 | 10/2006 | Weisenburgh, II et al. |
| 2006/0253069 A1 | 11/2006 | Li et al. |
| 2006/0276871 A1 | 12/2006 | Lamson et al. |
| 2007/0032785 A1 | 2/2007 | Diederich et al. |
| 2007/0038089 A1 | 2/2007 | Hatano et al. |
| 2007/0142846 A1 | 6/2007 | Catanese, III et al. |
| 2007/0179491 A1 | 8/2007 | Kratoska et al. |
| 2007/0197864 A1 | 8/2007 | Dejima et al. |
| 2007/0213703 A1 | 9/2007 | Naam et al. |
| 2008/0021484 A1 | 1/2008 | Catanese, III et al. |
| 2008/0021485 A1 | 1/2008 | Catanese, III et al. |
| 2008/0033232 A1 | 2/2008 | Catanese, III et al. |
| 2008/0033458 A1 | 2/2008 | McLean et al. |
| 2008/0033488 A1 | 2/2008 | Catanese, III et al. |
| 2008/0039833 A1 | 2/2008 | Catanese, III et al. |
| 2008/0039872 A1 | 2/2008 | Catanese, III et al. |
| 2008/0039874 A1 | 2/2008 | Catanese, III et al. |
| 2008/0039875 A1 | 2/2008 | Catanese, III et al. |
| 2008/0039876 A1 | 2/2008 | Catanese, III et al. |
| 2008/0039893 A1 | 2/2008 | McLean et al. |
| 2008/0039894 A1 | 2/2008 | Catanese, III et al. |
| 2008/0046045 A1 | 2/2008 | Yon et al. |
| 2008/0110457 A1 | 5/2008 | Barry et al. |
| 2008/0132826 A1 | 6/2008 | Shadduck et al. |
| 2008/0188811 A1 | 8/2008 | Kim |
| 2008/0208187 A1 | 8/2008 | Bhushan et al. |
| 2008/0214956 A1 | 9/2008 | Briggs et al. |
| 2008/0217325 A1 | 9/2008 | Von Buren et al. |
| 2008/0249399 A1 | 10/2008 | Appling et al. |
| 2008/0262491 A1 | 10/2008 | Swoyer et al. |
| 2008/0269737 A1 | 10/2008 | Elmouelhi et al. |
| 2008/0269862 A1 | 10/2008 | Elmouelhi et al. |
| 2008/0275440 A1 | 11/2008 | Kratoska et al. |
| 2008/0297287 A1 | 12/2008 | Shachar et al. |
| 2008/0312497 A1 | 12/2008 | Elmouelhi et al. |
| 2008/0312521 A1 | 12/2008 | Solomon |
| 2009/0018553 A1 | 1/2009 | McLean et al. |
| 2009/0054871 A1 | 2/2009 | Sharkey et al. |
| 2009/0138001 A1 | 5/2009 | Barry et al. |
| 2009/0149846 A1 | 6/2009 | Hoey et al. |
| 2009/0199855 A1 | 8/2009 | Davenport |
| 2009/0216220 A1 | 8/2009 | Hoey et al. |
| 2009/0227998 A1 | 9/2009 | Aljuri et al. |
| 2009/0306640 A1 | 12/2009 | Glaze et al. |
| 2010/0016757 A1 | 1/2010 | Greenburg et al. |
| 2010/0049031 A1 | 2/2010 | Fruland et al. |
| 2010/0060328 A1 | 3/2010 | Ingman et al. |
| 2010/0094270 A1 | 4/2010 | Sharma |
| 2010/0114083 A1 | 5/2010 | Sharma |
| 2010/0179416 A1 | 7/2010 | Hoey et al. |
| 2010/0193568 A1 | 8/2010 | Scheib et al. |
| 2010/0204688 A1 | 8/2010 | Hoey et al. |
| 2010/0256636 A1 | 10/2010 | Fernandez et al. |
| 2010/0262133 A1 | 10/2010 | Hoey et al. |
| 2010/0262137 A1 | 10/2010 | Nye et al. |

(56) References Cited

U.S. PATENT DOCUMENTS

| | | |
|---|---|---|
| 2010/0292767 A1 | 11/2010 | Hoey et al. |
| 2010/0298948 A1 | 11/2010 | Hoey et al. |
| 2011/0060328 A1 | 3/2011 | Skwarek et al. |
| 2011/0077628 A1 | 3/2011 | Hoey et al. |
| 2011/0106072 A1 | 5/2011 | Sundquist et al. |
| 2011/0160648 A1 | 6/2011 | Hoey |
| 2011/0264176 A1 | 10/2011 | Jackson et al. |
| 2011/0319759 A1 | 12/2011 | Liu et al. |
| 2012/0259271 A1 | 10/2012 | Shadduck et al. |
| 2012/0265276 A1 | 10/2012 | Curley |
| 2013/0006231 A1 | 1/2013 | Sharma et al. |
| 2013/0066308 A1 | 3/2013 | Landman |
| 2013/0072855 A1 | 3/2013 | Sherry et al. |
| 2013/0074847 A1 | 3/2013 | Hoey et al. |
| 2013/0172867 A1 | 7/2013 | Shadduck et al. |
| 2013/0253622 A1 | 9/2013 | Hooven |
| 2013/0261692 A1 | 10/2013 | Cardinal et al. |
| 2014/0039356 A1 | 2/2014 | Sachs et al. |
| 2014/0200568 A1 | 7/2014 | Sharma |
| 2014/0276713 A1 | 9/2014 | Hoey et al. |
| 2014/0354381 A1 | 12/2014 | Kohlhafer |
| 2015/0025515 A1 | 1/2015 | Hoey et al. |
| 2015/0126990 A1 | 5/2015 | Sharma et al. |
| 2015/0157384 A1 | 6/2015 | Hoey et al. |
| 2016/0015445 A1 | 1/2016 | Hoey et al. |
| 2016/0081736 A1 | 3/2016 | Hoey et al. |
| 2016/0220296 A1 | 8/2016 | Hastings et al. |
| 2016/0270838 A1 | 9/2016 | Hastings et al. |
| 2016/0331435 A1 | 11/2016 | Hoey et al. |
| 2017/0056089 A1 | 3/2017 | Hoey et al. |

FOREIGN PATENT DOCUMENTS

| | | |
|---|---|---|
| CN | 101072544 | 11/2007 |
| CN | 101257855 | 9/2008 |
| CN | 101006939 A | 11/2008 |
| CN | 101491458 A | 7/2009 |
| CN | 101554498 A | 10/2009 |
| CN | 101690834 A | 4/2010 |
| CN | 101803947 A | 8/2010 |
| CN | 103917200 A | 7/2014 |
| CN | 105208939 A | 12/2015 |
| CN | 105873534 | 8/2016 |
| CN | 105944188 A | 9/2016 |
| JP | 7-507696 A | 8/1995 |
| JP | 8-501957 A | 3/1996 |
| JP | 8-504613 A | 5/1996 |
| JP | 11-318925 A | 11/1999 |
| JP | 200014663 A | 1/2000 |
| JP | 2000005191 A | 1/2000 |
| JP | 2001500763 A | 1/2001 |
| JP | 2005137916 A | 6/2005 |
| JP | 2016515863 A | 6/2016 |
| JP | 2020-505093 A | 2/2020 |
| WO | 92/10142 A1 | 6/1992 |
| WO | 9921481 A2 | 5/1999 |
| WO | 9944657 A1 | 9/1999 |
| WO | 01/24715 A1 | 4/2001 |
| WO | 02069821 A1 | 9/2002 |
| WO | 03/088851 A1 | 10/2003 |
| WO | 03/096871 A2 | 11/2003 |
| WO | 2006/004482 A1 | 1/2006 |
| WO | 2008/083407 A1 | 7/2008 |
| WO | 2010054237 A1 | 5/2010 |
| WO | 2010/080467 A2 | 7/2010 |
| WO | 2013/160772 A2 | 10/2013 |
| WO | 2017/106843 A1 | 6/2017 |

OTHER PUBLICATIONS

Hoey et al.; U.S. Appl. No. 15/851,333 entitled "Vapor ablation systems and methods," filed Dec. 21, 2017.

Hai; Photoselective Vaporization Prostatectomy: A Palliative Treatment Option for Men with Urinary Obstruction Secondary ta Prostate Cancer; PCRI Prost.Cancer Rsrch.Inst. Reprint.from PCRI Insights Nov. 2005, val8(4); Dwnld from http://www.prostate-cancer.org/pcricmsinade/233 on May 10, 2012; 4 pages.

Nguyen et al; Updated results of magnetic resonance imaging guided partial prostate brachytherapy for favorable risk prostate cancer: implications for focal therapy; J. Urol.; 188(4); pp. 1151-1156; Oct. 2012.

Hoey et al.; U.S. Appl. No. 15/900,295 entitled "Systems and methods for prostate treatment," filed Feb. 20, 2018.

* cited by examiner

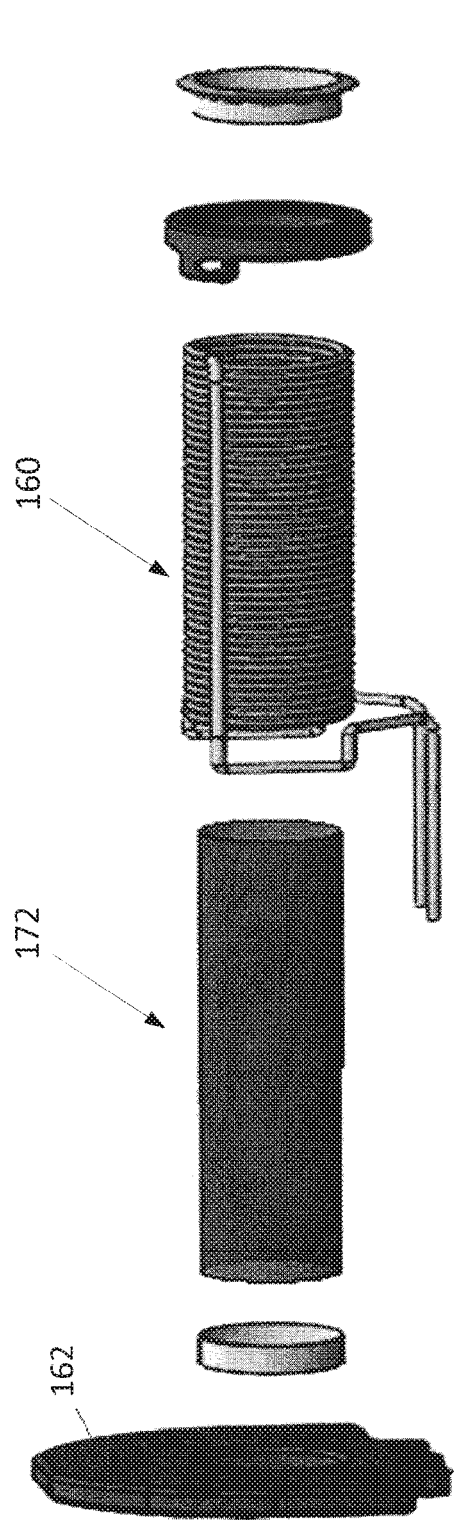
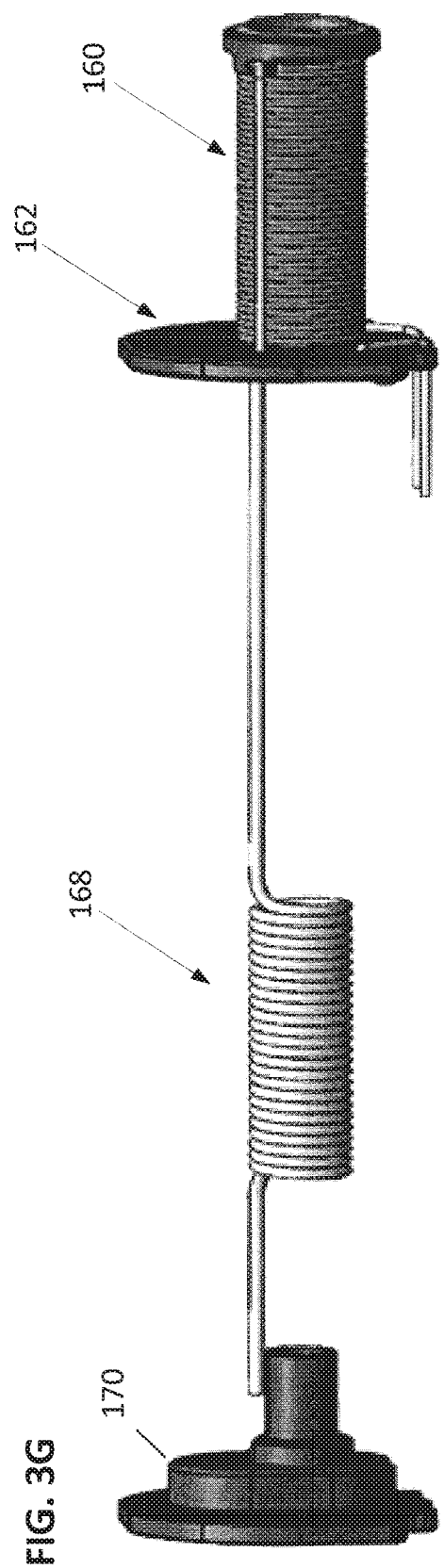
FIG. 3F
FIG. 3G

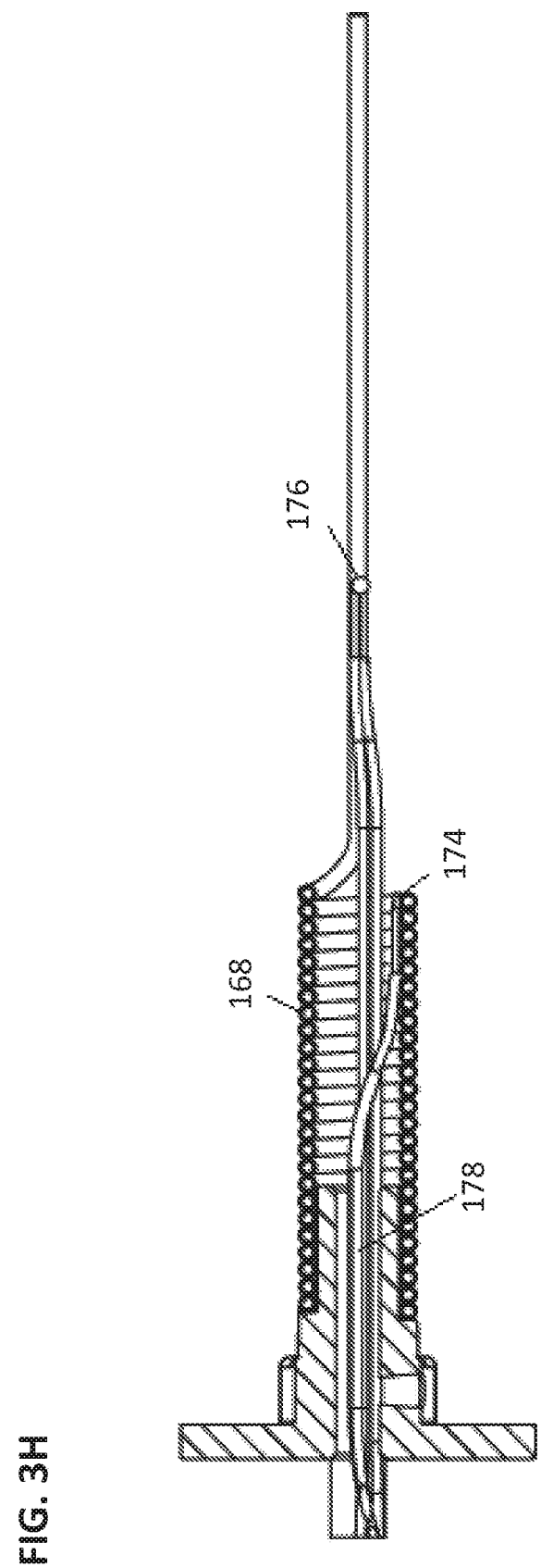

MEDICAL DEVICES AND METHODS

CROSS REFERENCE TO RELATED APPLICATIONS

This application is a continuation of U.S. application Ser. No. 15/864,957, filed Jan. 8, 2018, now U.S. Pat. No. 10,751,107, which claims the benefit of priority to U.S. Provisional Application No. 62/443,555, filed Jan. 6, 2017, which are herein incorporated by reference in their entireties.

This application is related to U.S. application Ser. No. 14/773,853, filed Sep. 9, 2015, and International Application No. PCT/US2016/067558, filed Dec. 19, 2016, both of which are herein incorporated by reference in their entireties.

INCORPORATION BY REFERENCE

All publications, including patents and patent applications, mentioned in this specification are herein incorporated by reference in their entirety to the same extent as if each individual publication was specifically and individually indicated to be incorporated by reference.

FIELD

The present invention relates to devices and related methods for treatment of the prostate using a minimally invasive approach.

BACKGROUND

The prostate early in life is the size and shape of a walnut and prior to the enlargement resulting from BPH, weighs about 20 grams. Prostate enlargement appears to be a normal process. With age, the prostate gradually increases in size to twice or more its normal size. The fibromuscular tissue of the outer prostatic capsule restricts expansion after the gland reaches a certain size. Because of such restriction on expansion, the intracapsular tissue will compress against and constrict the prostatic urethra, thus causing resistance to urine flow.

The prostate can be classified into three zones: the peripheral zone, transition zone, and central zone. Peripheral zone (PZ) comprises about 70% of the volume of a male's prostate. This sub-capsular portion of the posterior aspect of the prostate gland surrounds the distal urethra and 70 to 80% of cancers originate in the peripheral zone tissue. The central zone (CZ) surrounds the ejaculatory ducts and contains about 20-25% of the prostate volume. The central zone is often the site of inflammatory processes. The transition zone (TZ) is the site in which benign prostatic hyperplasia develops, and contains about 5-10% of the volume of glandular elements in a normal prostate, but can constitute up to 80% of such volume in cases of BPH. The transition zone includes two lateral prostate lobes and the periurethral gland region. There are natural barriers around the transition zone, i.e., the prostatic urethra, the anterior fibromuscular stroma FS, and a fibrous plane FP between the transition zone and peripheral zone. The anterior fibromuscular stroma FS or fibromuscular zone is predominantly fibromuscular tissue.

Approximately 70% to 80% of prostate cancers originate in the peripheral zone of the prostate and may be confined to the peripheral zone. In recent years, there has been an increased interest in focal therapy for prostate cancer, treating only regions of tissue in which cancer has been found following biopsies. Prior art focal therapy treatments, such as with RF ablation energy, may not confine the treatment to the peripheral zone tissue.

SUMMARY OF THE DISCLOSURE

Systems and methods for ablating peripheral zone tissues without ablating non-peripheral zone tissues are disclosed. A transperineal approach uses a vapor delivery device to access and treat peripheral zone tissues.

Vapor may be delivered at multiple sites along the path of the needle using ultrasound and needle position sensor guidance.

The vapor delivery needle can be capable of controlled movement along its path, including stopping to deliver vapor. Systems and methods for controlling the movement of the needle in digital steps to any location within its reach are disclosed.

Most prostate cancer arises in the peripheral zones. Vapor delivered through a needle to the peripheral zone will not cross tissue barriers to other zones of the prostate, where cancer may not be present.

A method of treating prostate cancer in a patient is provided, comprising cooling a urethra of the patient with a urethral cooling catheter, cooling tissue adjacent to a prostate of the patient with an injection of chilled fluid, imaging the prostate in real-time, advancing a vapor delivery device trans-perineally into the prostate, inductively generating vapor in the vapor delivery device, and delivering the vapor to the prostate through the vapor delivery device.

In some examples, the method further comprises measuring a first electrical impedance and phase shift of tissue at a distal tip of the vapor delivery device. The method can further determine if the distal tip is inserted into the prostate of the patient based on the measured first electrical impedance and phase shift.

Additionally, the method can measure a second electrical impedance and phase shift of tissue at a portion of the vapor delivery device proximal to the distal tip, and determine if the portion of the vapor delivery device proximal to the distal tip is inserted into the prostate of the patient based on the measured second electrical impedance and phase shift.

The method can further include actively insulating a portion of the vapor delivery device that lies adjacent to perineum tissue of the patient. The active insulation can be used to protect sensitive tissues from the heated vapor delivery device. The actively insulating step can comprise forming an insulating air space in a plurality of tubes surrounding an elongate shaft of the vapor delivery device.

A method of positioning a vapor delivery device in a prostate is also provided, comprising advancing a vapor delivery device trans-perineally into the prostate, measuring a first electrical impedance and phase shift of tissue contacting a tip electrode of the vapor delivery device, measuring a second electrical impedance and phase shift of tissue contacting a ring electrode of the vapor delivery device, the ring electrode being proximal to the tip electrode, determining if the tip electrode and the ring electrode are disposed within the prostate, and delivering vapor to the prostate if the tip electrode and ring electrode are disposed within the prostate.

The method can comprise applying an alternating current with a frequency between 1-100 MHz to determine an operating frequency that optimizes an impedance and phase contrast between tissues within and outside the prostate.

Additionally, the method can further comprise providing an indication to the user that the tip electrode and the ring electrode are disposed within the prostate.

A vapor delivery device is also provided, comprising an elongate shaft, a distal tip electrode configured to measure a first electrical impedance and phase shift of tissue contacting the distal tip electrode, a ring electrode disposed proximally on the elongate shaft from the distal tip electrode, the ring electrode configured to measure a second electrical impedance and phase shift of tissue contacting the ring electrode, an electrically insulative portion disposed between the distal tip electrode and the ring electrode, and an electronic controller configured to determine if the tip electrode and the ring electrode are disposed within the prostate based on the first and second electrical impedance and phase shift.

The device can further include a circuit configured to supply an alternating current with a frequency between 1-100 MHz to determine an operating frequency that optimizes an impedance and phase contrast between tissues within and outside the prostate.

A vapor delivery system is also provided, comprising a RF generator console, a syringe adapted to be inserted into the RF generator console, the syringe comprising a syringe handle, a plunger, a handle magnet disposed on the syringe handle, and a plunger magnet disposed in the plunger, a source of fluid coupled to the syringe, and a generator magnet disposed in the RF generator and configured to align with the plunger magnet to advance and retract the plunger magnet, wherein the RF generator console is configured to automatically refill the syringe with fluid from the source of fluid by advancing and retracting the generator magnet.

In one example, the system further comprises a one-way check valve configured to allow fluid to flow from the source of fluid into the syringe, and optionally a second one-way check valve configured to allow fluid to flow from the syringe to a vapor delivery device.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

FIGS. 3A, 3B, 3C, 3D, 3E, 3F, 3G and 3H show a vapor generator for use with the delivery system.

DETAILED DESCRIPTION OF THE INVENTION

Figure 1A:
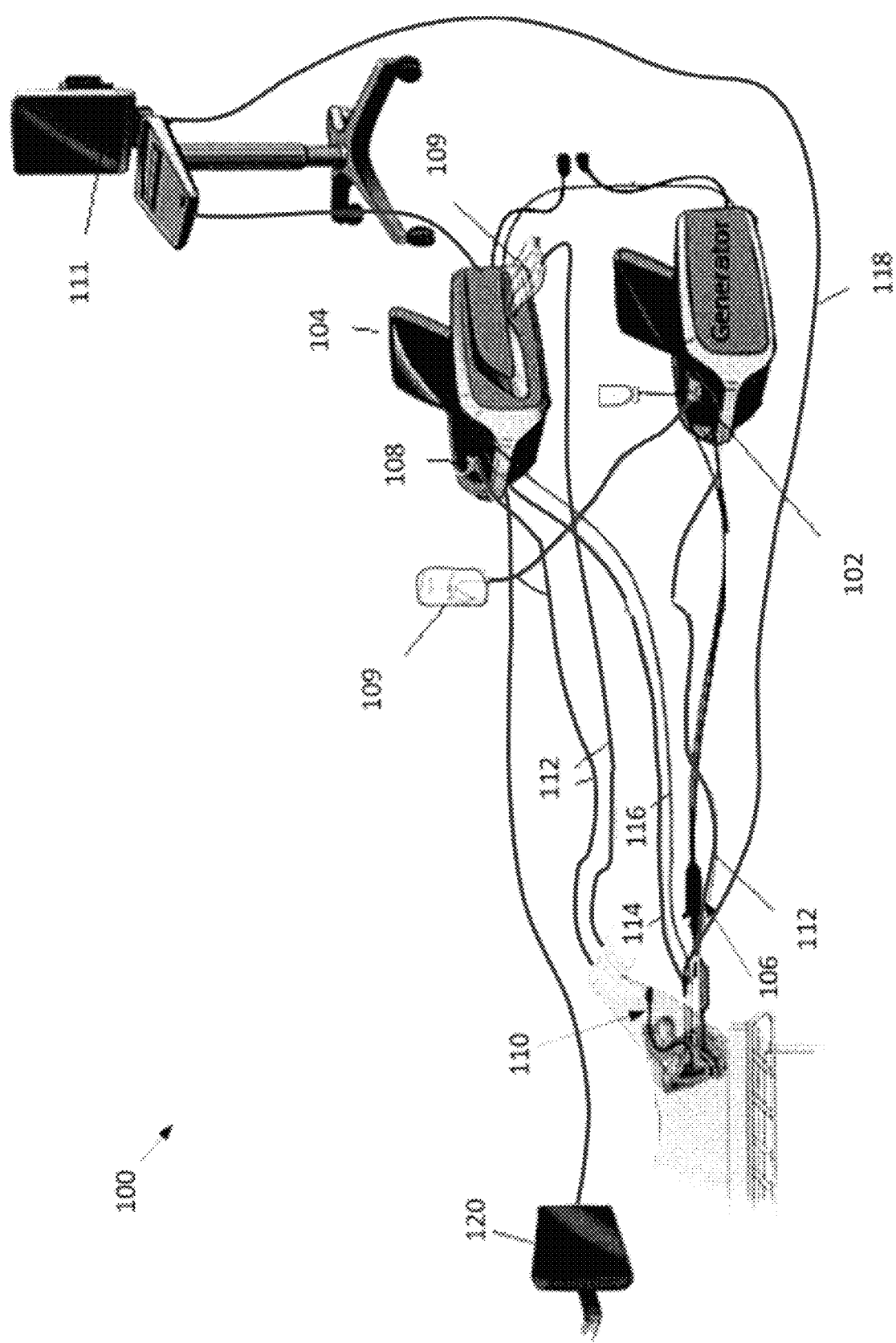
FIGS. 1A-1B show a trans-perineal vapor delivery system.

A trans-perineal vapor delivery system is provided for treatment of prostate cancer. As illustrated in FIG. 1A, the trans-perineal vapor delivery system 100 comprises a RF generator 102, auxiliary controller console 104, a vapor generation and delivery handle 106, vapor delivery needle (not shown), cooling needle (not shown) for delivery of saline to cool and protect nerves around the outside of the prostate, thermocouple needle (not shown) that further protect the nerves and other periprostatic tissues by alerting the user of high temperatures, a urethral cooling system 108 that circulates cooled saline 109 through a cooling catheter 110 placed in the prostatic urethra to protect this tissue, and an ultrasound imaging system 111 such as a trans-rectal ultrasound (TRUS) imaging system. The system can further include saline lines 112, thermocouple lines 114 and 116, and imaging lines 118 to connect the cooling system, thermocouple needles, and ultrasound imaging system, respectively. Images from the ultrasound imaging system 111 can be displayed on display 120.

Figure 1B:
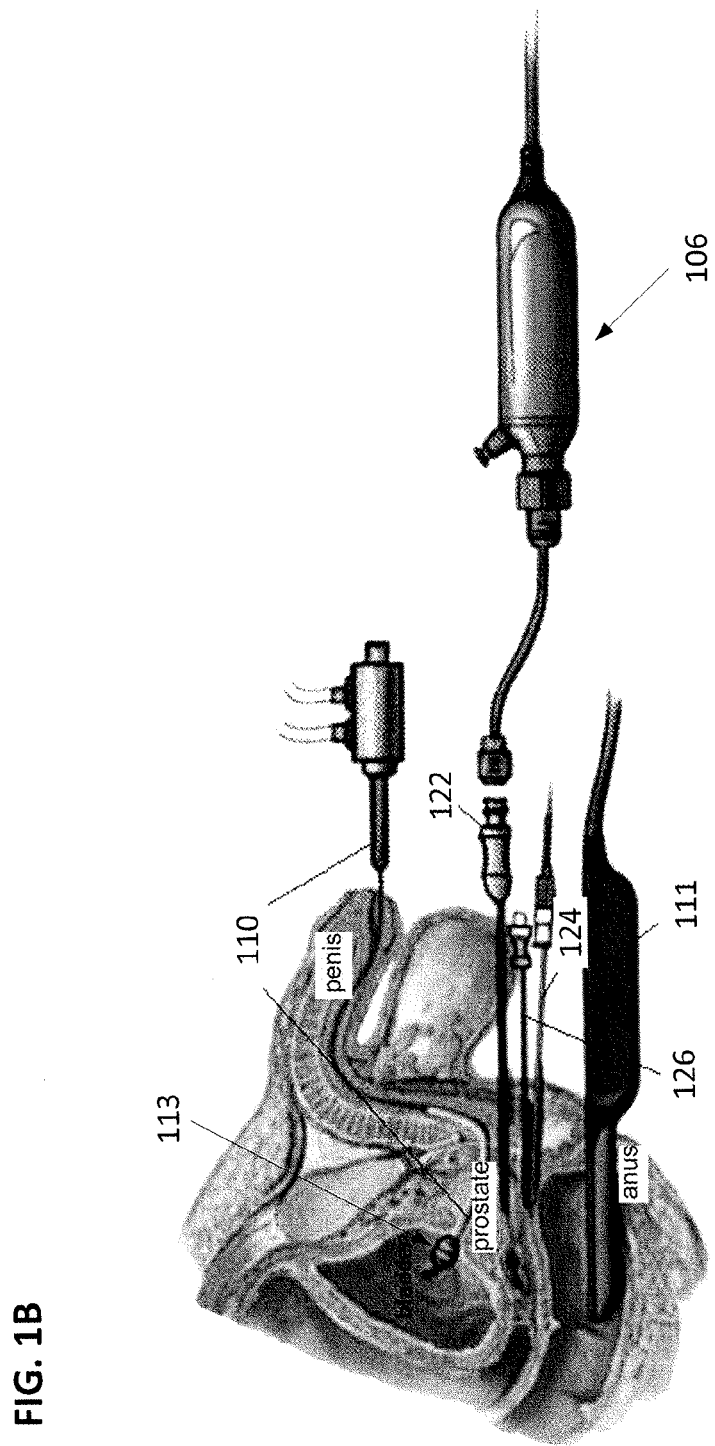

FIG. 1B is a close-up view of the vapor generation and delivery handle 106, the vapor delivery needle 122, cooling needle 124, thermocouple needle 126, cooling catheter 110, and the ultrasound imaging system 111. The vapor delivery needle 122 is configured for trans-perineal insertion into the prostate to deliver a heated condensable vapor into the prostate to treat prostate cancer. The cooling needle 124, along with the cooling catheter, are configured to deliver a cooled saline into the tissue proximate the prostate to prevent ablation damage to adjacent tissues such as the urethra and anus. The thermocouple needle 126 is configured to measure the temperature of the tissue including the tissue of the prostate during vapor delivery.

The primary function of the RF generator is to provide sterile water and RF power to the vapor delivery device heating element. The RF generator delivers vapor when the operator pushes the vapor delivery button on the delivery device. The RF generator also provides saline to needles for infusion into tissue surrounding the prostate. The saline provides cooling, but also serves to fill space and provide separation between the prostate and sensitive rectal tissues during therapy delivery.

The auxiliary controller console in FIG. 1A contains a custom designed Peltier effect chiller for circulating cooled saline through a custom designed urethral cooling catheter seen in the prostatic urethra in FIG. 1B. Saline for the chiller is provided from a saline bag reservoir, which also supplies saline to the RF generator for delivery through saline infusion needles to tissues outside the prostate. The auxiliary controller console also tracks the temperature at multiple points outside of the prostate to ensure that temperatures that could damage periprostatic tissues are not exceeded.

The auxiliary controller console shown in FIG. 1A chills and circulates water to cool the urethra during therapy. It also monitors temperatures at the locations of thermocouples along the length of needles inserted into tissue outside the prostate, and prevents therapy delivery when any temperature exceeds specified bounds. Each thermocouple needle contains three or more thermocouples spaced along its length. In addition, the auxiliary controller console monitors the electrical impedance and phase shift at the vapor delivery tip and ring electrodes, and interacts with the operator to determine whether the vapor delivery needle tip is adjacent prostate tissue before delivering therapy. A custom display of the status of tissue adjacent the needle tip can be merged onto the real-time ultrasound imaging in the auxiliary controller, and displayed on the monitor in the work zone at a location preferred by the operator, as illustrated in FIG. 1A.

RF Generator

The requirements for a cancer vapor therapy system, that may deliver many doses of vapor at higher rates and over longer periods of time than a BPH system, include delivering adequate power to a larger total volume of sterile water. The system of FIGS. 1A-1B can provide up to 500 Watts of RF power at a frequency in the range of 300 to 600 kHz.

One solution to providing larger amounts of sterile water for steam generation is to use a large vapor syringe in the RF generator. This solution requires a linear motor to drive the syringe plunger that moves at a lower speed for a given water flow rate. It can be difficult to ensure a precise water flow rate at reduced plunger speeds. In addition, the compliance of the syringe may increase for larger diameter syringes, also reducing the accuracy of water delivery. The syringe length is limited by the length of the RF generator, which is limited by clinical needs.

Figure 2A:
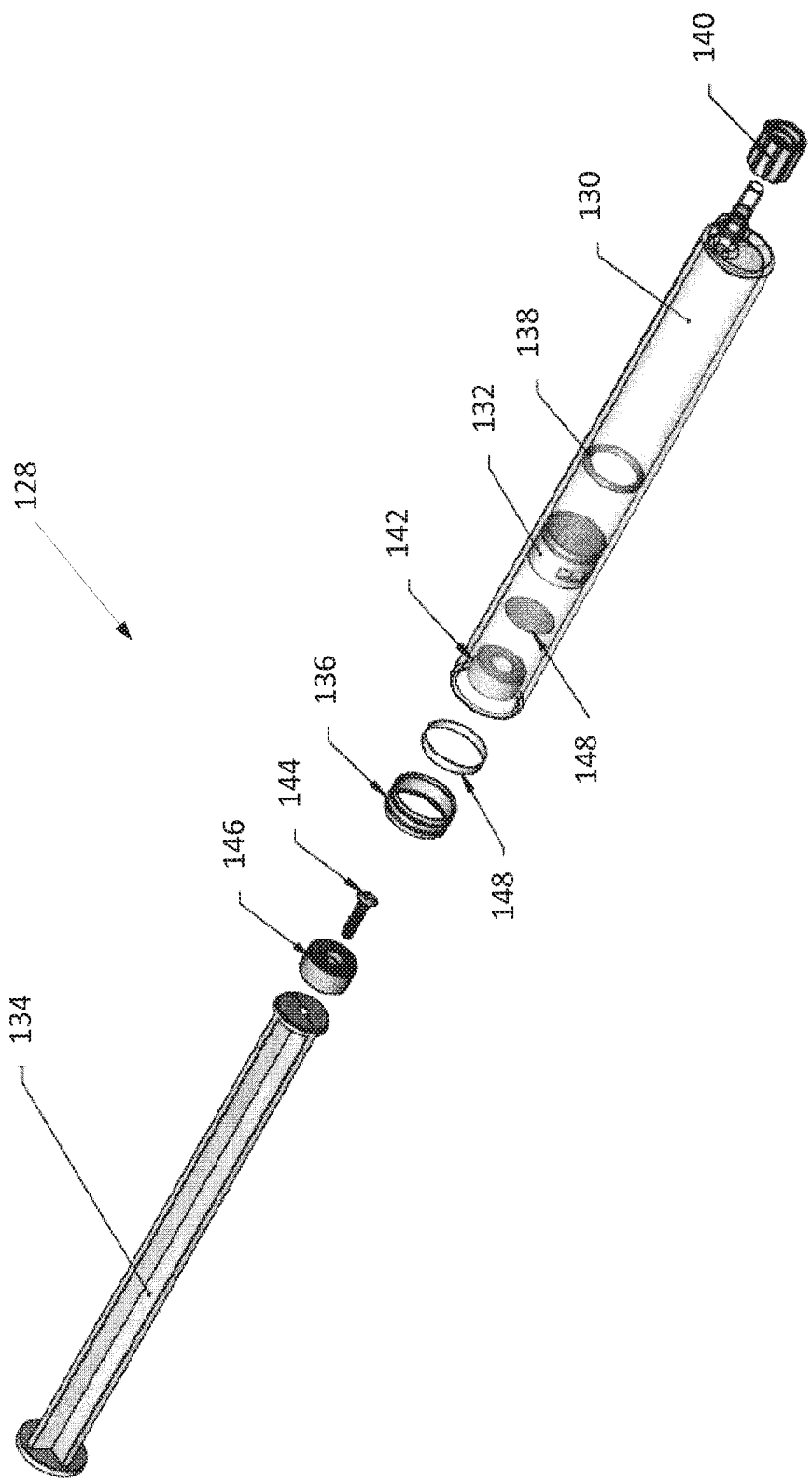
FIGS. 2A, 2B and 2C show a syringe for use with the delivery system.

To overcome the need for more water, this disclosure provides a sterile water syringe that refills automatically when it runs out of water. The syringe is shown as an assembly drawing in FIG. 2A and assembled in FIG. 2B. In FIG. 2A, sterile water syringe 128 comprises syringe barrel 130, syringe plunger 132, syringe handle 134, bushing 136, o-ring 138, luer fitting 140, syringe plunger magnet 142, screw 144, handle magnet 146, and adhesives 148.

Figure 2B:
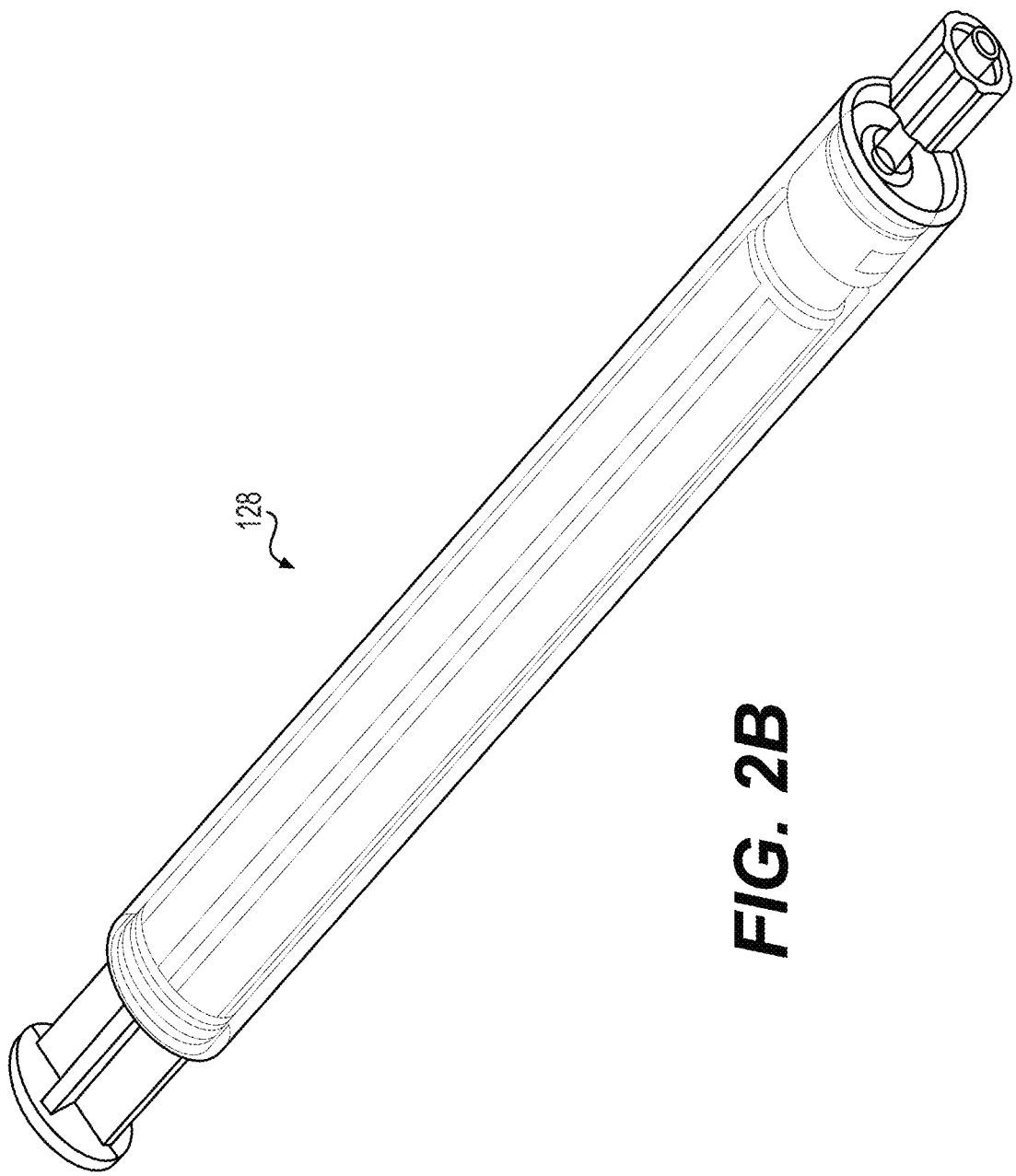
Figure 2C:
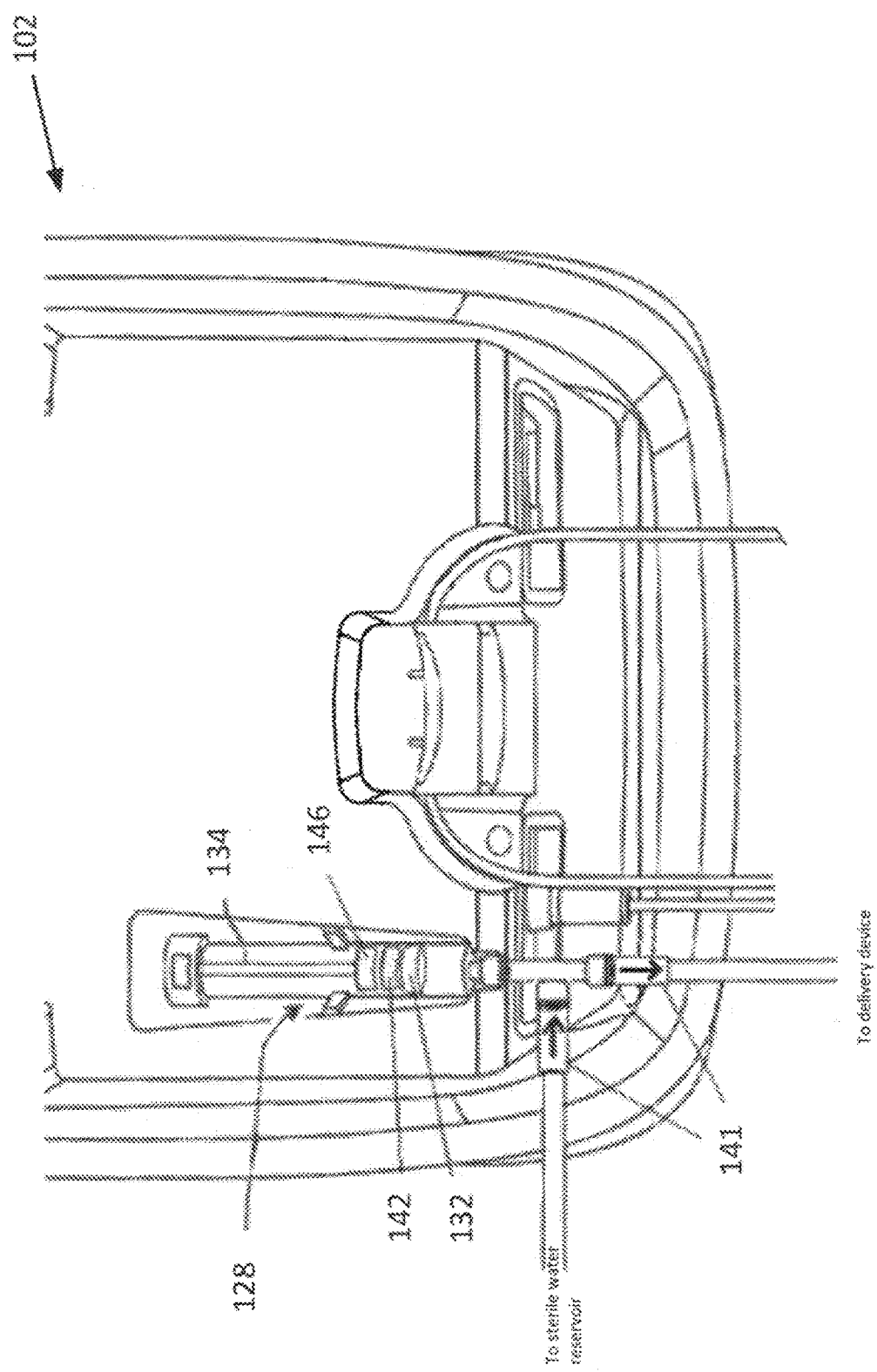

FIG. 2C shows the sterile water syringe 128 inserted into the RF generator 102, and further shows syringe handle 134, syringe plunger magnet 142, handle magnet 146, syringe plunger 132. The sterile water syringe can be attached to the vapor generator within the delivery handle through a water line containing a one-way check valve 141 that allows water flow into but not out of the delivery device, and a second one-way valve 141 that allows water to flow from but not into a sterile water reservoir. At the end of a procedure, the operator disengages the sterile water syringe by pulling to overcome the magnetic attraction between the syringe plunger magnet and the RF generator shaft plunger magnet.

The manually operated plunger 132 and handle 134 shown in FIGS. 2A-2C engages the syringe barrel through magnetic attraction between the handle magnet 146 and syringe plunger magnet 142. The operator fills the syringe by placing it in sterile water and pulling back to fill. The operator can then disengage the handle by pulling on it to overcome the magnetic attraction. When the filled syringe is inserted into the RF generator, a magnet (identical to magnet 146, not shown since it is inside the RF generator) aligned with the syringe plunger shaft within the RF generator engages the syringe plunger magnet, enabling the system to both advance and retract the syringe.

To set up and prime the system, the operator is instructed to perform the following steps: 1) Manually fill the vapor syringe with saline and place into RF generator, engaging the magnets. 2) Attach a two way luer to the syringe having: a one way valve OUT to vapor generation and delivery handle, a one way valve IN from a sterile water reservoir. 3) Engage the delivery device therapy delivery button to cause the RF generator to drive the plunger to deliver sterile water to prime the system, and to deliver RF power to produce steam. 4) After which the generator retracts the plunger, enabled by magnetic attraction between the shaft plunger magnet and the syringe plunger magnet. A one way valve prevents water in the delivery line from returning to the syringe. The second one way valve allows water from the reservoir to refill the syringe as the plunger retracts. 5) After which the generator plunger shaft moves forward until it senses a 5 lb. positive pressure, indicating that the plunger is engaged and is delivering water to the delivery system. 6) Engage the delivery device therapy delivery button to deliver a test shot of vapor into the air, after which the system enters the low-power idle state, awaiting therapy delivery. 7) Following therapy deliveries, if the syringe plunger moves to the end of the syringe, the refill sequence is automatically triggered and the plunger retracts. 8) The operator can refill the syringe at any time by pressing a button on the generator screen. In some embodiments, the initial filling of the syringe, step 1) is done automatically. In this mode the operator places an empty syringe into the generator, attaches the two-way luer fitting to the syringe, and the initial filling of the syringe is performed automatically by the system.

Vapor Delivery Device

Figure 3A:
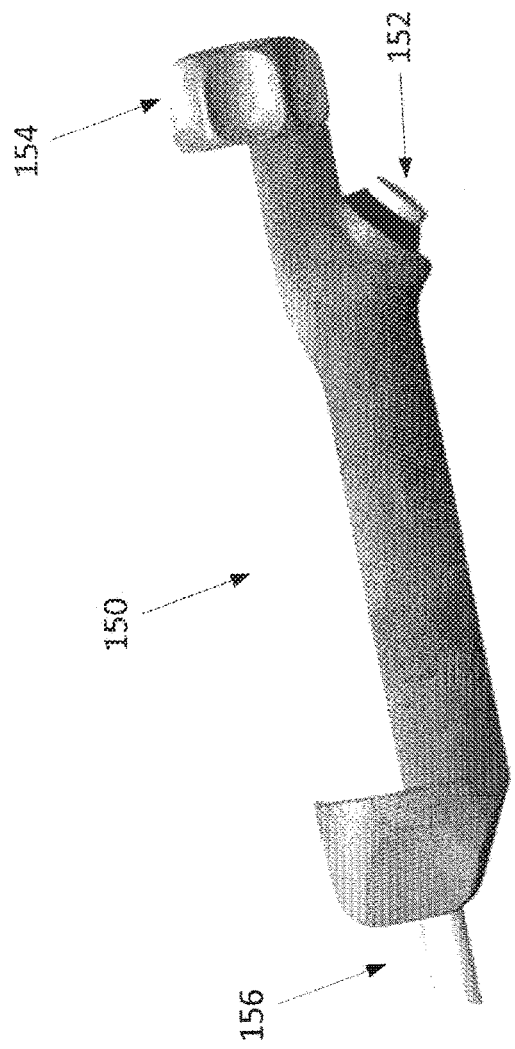
Figure 3B:
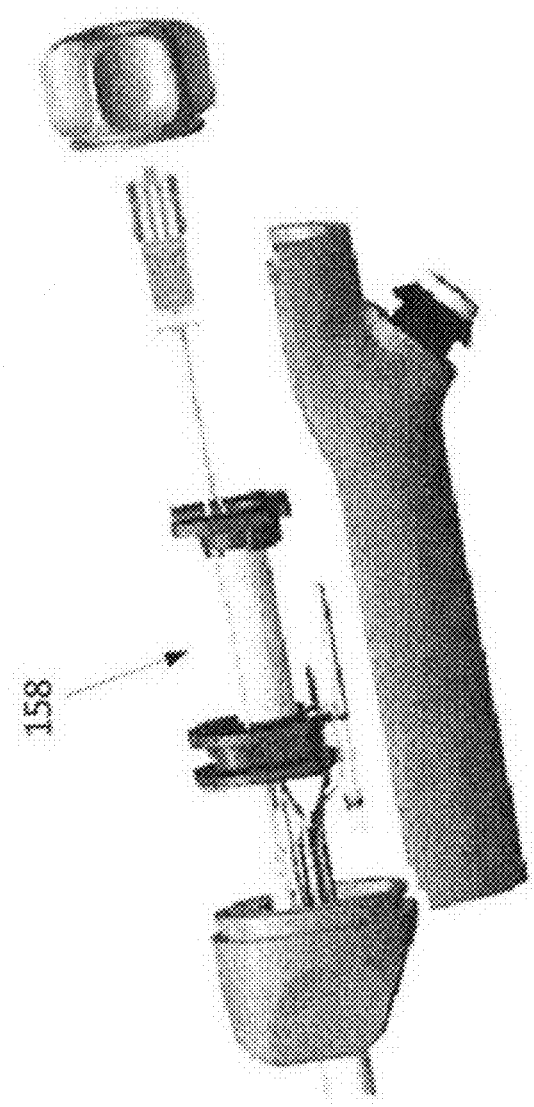

The vapor generation and delivery handle 106 shown in FIGS. 3A-3B includes a handle portion 150, a therapy delivery button 152, a luer fitting 154 for the vapor delivery needle, and a cable and connector 156 to connect the vapor generation and delivery handle to the RF generator. As shown in FIG. 3B, the vapor generation and delivery handle further includes a heating element 158 that has a RF coil of Litz wire with extruded high temperature PFA insulation and an Inconel 625 inner coil with coil and outlet thermocouples, and a Luer fitting that attaches to needles placed in the patient.

The heating element 158 in the vapor delivery device can handle high temperatures for prolonged therapies at up to 500 Watts. The heating element can comprise an outer RF coil of wire and an inner coil of vapor tubing. When RF current is applied to the outer RF coil, it inductively heats fluid flowing through the inner coil of vapor tubing.

The inner coil of vapor tubing and the outer RF coil structure can be cantilevered from the water input end so that no materials are exposed to the hot vapor end of the inner coil of vapor tubing. The Inconel 625 inner coil can include micro welds between the windings along two sides of the coil. This ensures that winding separation, and consequent changes in therapy delivery, cannot occur. The handle is moved between pre-inserted vapor delivery needles, as shown in FIG. 1B, for therapy.

Figure 3C:
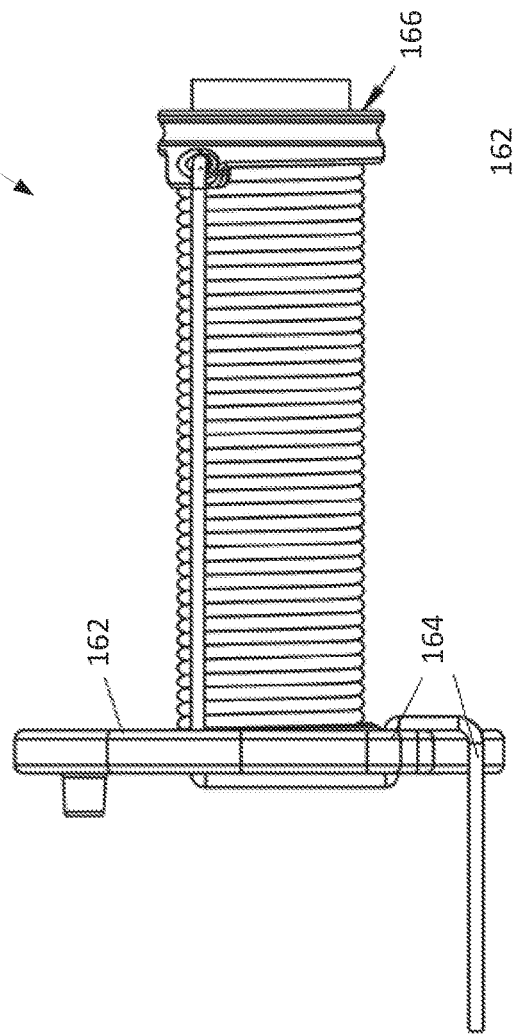
Figure 3D:
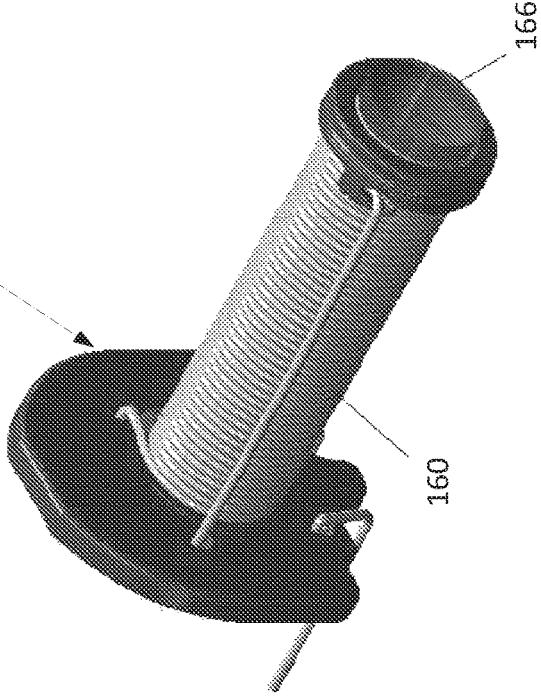

The heating element outer RF coil 160 is shown in FIGS. 3C-3D. The heating element can include an RF coil mounting fixture 162. In a preferred embodiment, the outer RF coil is comprised of individually enameled 44 gauge copper wire strands having an overall equivalent #24 wire gauge. The 44 gauge stranding is appropriate for avoiding skin effect issues at an operating frequency in the 350 to 850 kHz range and more specifically in the preferred range of 440 to 480 kHz. The Litz wire has an overall extruded 0.002" thick coating of PFA (perfluoroalkoxy) insulation. The insulation is rated for continuous use temperatures up to 250° C., which is especially important for windings adjacent the hot vapor end of the inner coil.

As an alternative to adhesive, the proximal end of the wire can be mechanically held in place by threading it through holes 164 in the RF coil mounting fixture. The distal wire is held in place by threading it through a hole in the wire retention ring 166 shown in FIG. 3B. The RF coil assembly break out is shown in FIG. 3C, which shows the RF coil wire wound on a thin wall, high temperature polyimide tube with attachment through the distal wire retention ring the RF coil mounting fixture. Both the go and return Litz wire leads to the coil are mechanically held in place by passing the wire through holes in the RF coil mounting fixture.

Figure 3E:
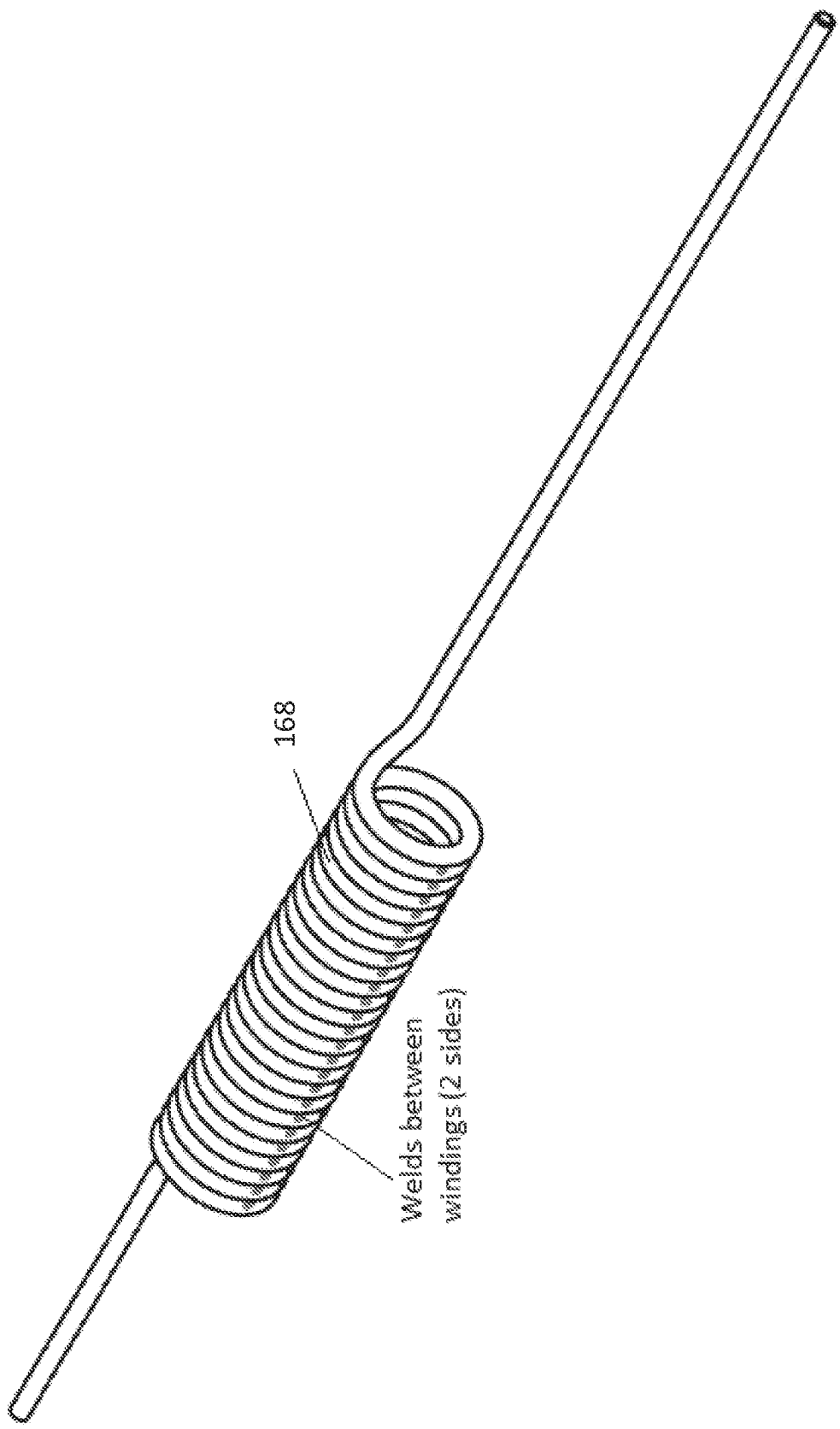

The inner coil of vapor tubing 168 is shown in FIG. 3E with two lines of micro welds, for example laser welds, between the windings. It is important to have good electrical contact between windings, which is insured by the welds.

The two lines of welds provide mechanical strength to help insure that the windings do not flex and thereby lose electrical contact.

FIG. 3F shows an exploded view of the outer RF coil 160, including high temperature polyimide tube 172 and RF coil mounting fixture 162. FIG. 3G shows the inner coil of vapor tubing cantilevered from the assembly hub 170. The inner coil of vapor tubing is inserted into the outer RF coil, but is shown separately from the RF coil in FIG. 3G for illustrative purposes. In this design, the distal end of the inner coil of vapor tubing contacts the high temperature polyimide tube 172, but does not contact other materials, which may not resist the high temperatures (up to 400° C.) that are possible, at least momentarily, when the distal end of the coil does not contain water.

The inner coil of vapor tubing can be constructed from Inconel 625, a non-magnetic stainless steel that has an electrical resistivity that is nearly independent of temperature over the range of temperatures encountered by the inner coil (20° C. to 400° C.). These properties insure consistent vapor and calorie delivery from shot to shot and device to device. In particular, 300 series stainless steels that are commonly used for hypo tubing have a residual magnetic permeability that can vary from lot to lot of tubing and can vary with thermal cycling. Variable permeability yields variable calorie output for a fixed generator input power. The electrical resistivity of 300 series stainless can change in an unpredictable way with thermal cycling, also yielding variable calorie output. These properties may be attributed to material phase changes between austenite and martinsite when the material is cold worked or thermally cycled.

The locations of the inner coil thermocouples is shown if FIG. 3H. The coil thermocouple 174 can be welded to the inside of the most distal coil winding. This is the hottest point on the inner coil because there may be little or no water at this location to vaporize and carry away heat. Yet this location is underneath the RF coil and is inductively heated. This is analogous to boiling water in a pan, which remains at the boiling temperature of water until the water has all boiled away, at which point its temperature rises quickly. The outlet thermocouple 176 is away from the RF coil, and receives heat input from the steam within the outlet tube and heat conducted from the vapor coil, where heat is applied, down the outlet tube to the thermocouple. Leads 178 can connect to the thermocouples and be routed through the interior of the inner coil of vapor tubing.

Vapor Delivery Needle

The prostate cancer vapor delivery needle needs to puncture the perineum, puncture the prostate capsule, and deliver vapor to only the prostate without burning the perineum tissue. These requirements are addressed in this invention by insulating a section of the needle that lies adjacent perineum tissue, and by measuring the electrical properties of tissue surrounding the tip to verify that the needle is in prostate tissue before delivering vapor.

A unique vapor delivery needle insulation system has been designed and implemented to prevent overheating of non-prostate tissues adjacent the needle. It includes an array of small polyimide tubes that surround the central vapor needle to provide an insulating air space between the hot needle and perineum tissues. A vacuum needle has also been developed.

The vapor delivery needle has two electrodes for sensing surrounding tissue electrical properties. The needle tip and a ring that is insulated from and proximal to the tip are the electrodes. A unique alarm system initially measures tissue electrical properties outside and within the prostate, and is thereafter able to determine whether the needle is inside or outside, and prevent vapor from being delivered outside of the prostate.

Figure 4A:
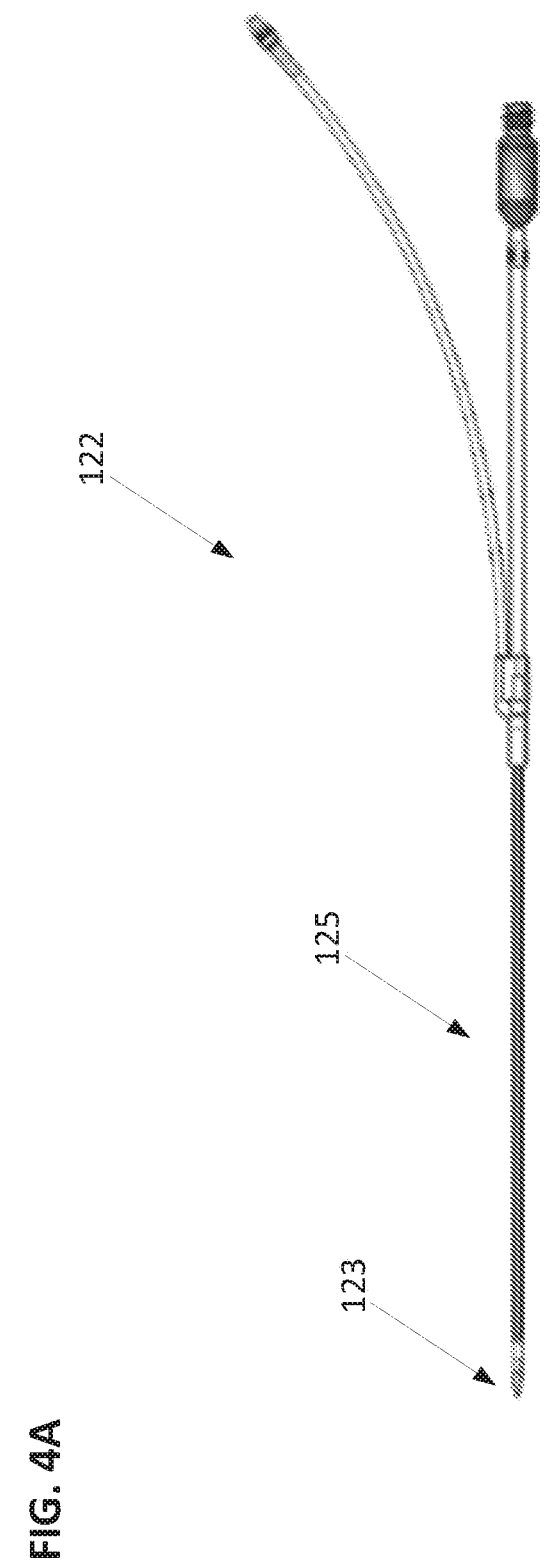
FIGS. 4A, 4B, 4C and 4D show a vapor delivery needle.
Figure 4B:
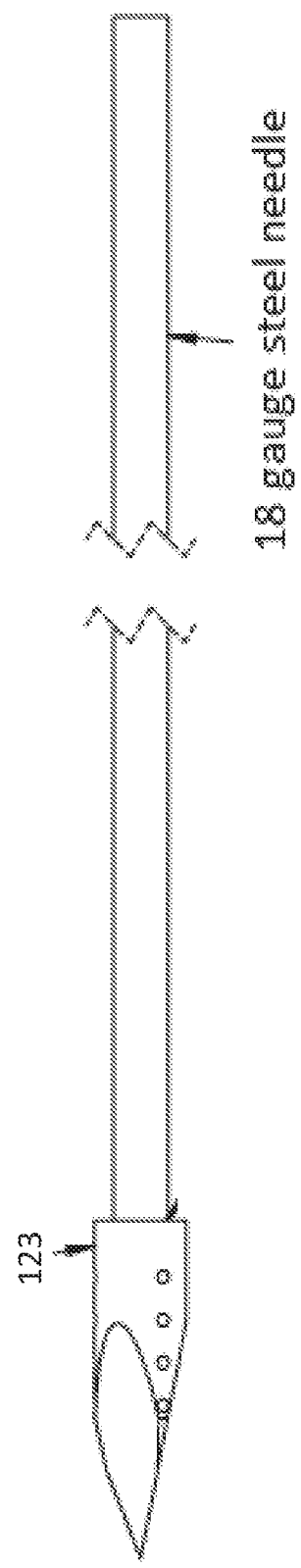
Figure 4C:
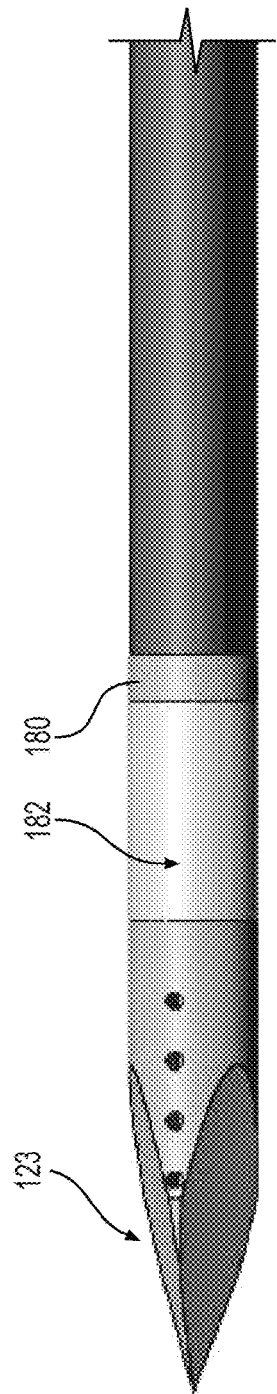

The vapor delivery needle 122 is shown in FIGS. 4A and 4C. The needle comprises a central hollow steel needle with shaped and sharpened tip 123, holes in the tip for delivering vapor to prostate tissues, a ring electrode 182 separated from the tip by an electrically insulating section 180, a thermally insulating section 125 that protects perineum tissue, leads with connector for the tip and ring electrodes, and a luer fitting to attach the needle to a vapor generation and delivery handle.

Figure 4D:
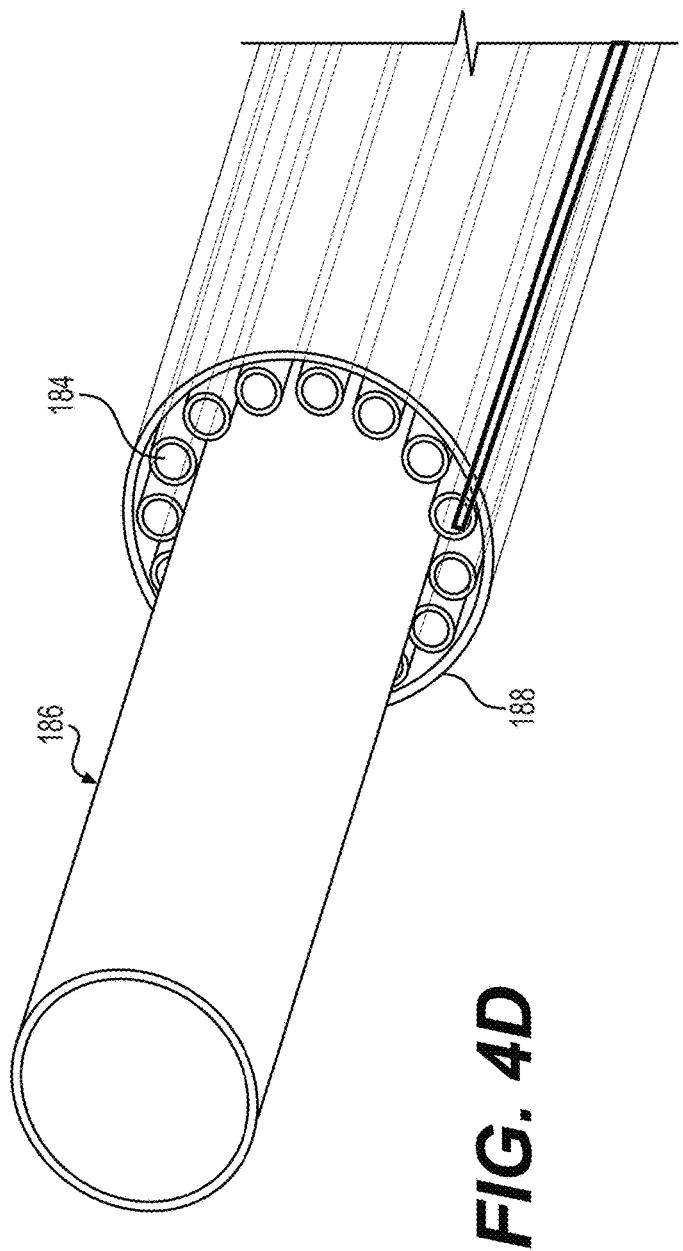

In one preferred embodiment, a vacuum is created between two concentric steel tubes to insulate the outside needle surface from hot vapor passing through the inside tube. In another preferred embodiment, shown in detail in FIG. 4D, thermal insulation is achieved using a circular array of air filled mini tubes 184 sandwiched between an inner tube 186 that covers the steel vapor tube and an outer tube 188 that contacts tissues of the perineum. The inner, outer and insulating tubes are preferably comprised of polyimide. Preferred dimensions for the three tubes in inches are:

| Description ID × Wall X OD | |
|---|---|
| .051 × .0025 × .056 | inner tube |
| .009 × .00075 × .0105 | mini tubes |
| .080 × .0025 × .085 | outer tube |

One of the tissue sensing electrodes can comprise of the needle tip itself which can be welded to the inner steel needle tube as shown in FIG. 4B. Electrical contact can be made at the proximal end of the inner steel needle with a lead passing through the electrical connector to the auxiliary controller console. The second electrode is the ring electrode shown in FIG. 4C, which is electrically insulated from the tip electrode by an insulating spacer. The ring electrode is electrically insulated from the steel needle inner tube by the inner polyimide tube. In a preferred embodiment, the lead for the ring electrode may pass through one of the mini tubes to the proximal electrical connector.

Biocapacitance Tissue Sensing and Guidance

In performing vapor therapy for prostate cancer, the physician is required to place the tip of the vapor delivery needle within the peripheral and/or transition zone of the patient's prostate. To do this, the needle is inserted through the patient's perineum and ultrasound guidance is utilized to navigate to the appropriate zone of the prostate. In some cases, multiple vapor treatments are performed using a single needle such that: the needle is placed in position, a treatment is performed, the needle is pulled back towards the apical end of the prostate or pushed forward towards the base of the prostate, and then, another treatment is performed. This process is repeated until a contiguous region of treated tissue is created about the axis of the needle.

If the emitter holes of the needle are fully contained within the prostate, the vapor delivered during the treatment will remain within the prostate because the prostate capsule is a convective barrier. If, however, one or more of the emitter holes is external to the prostate capsule, the vapor will travel outside of the prostate, which is undesirable.

Figure 5:
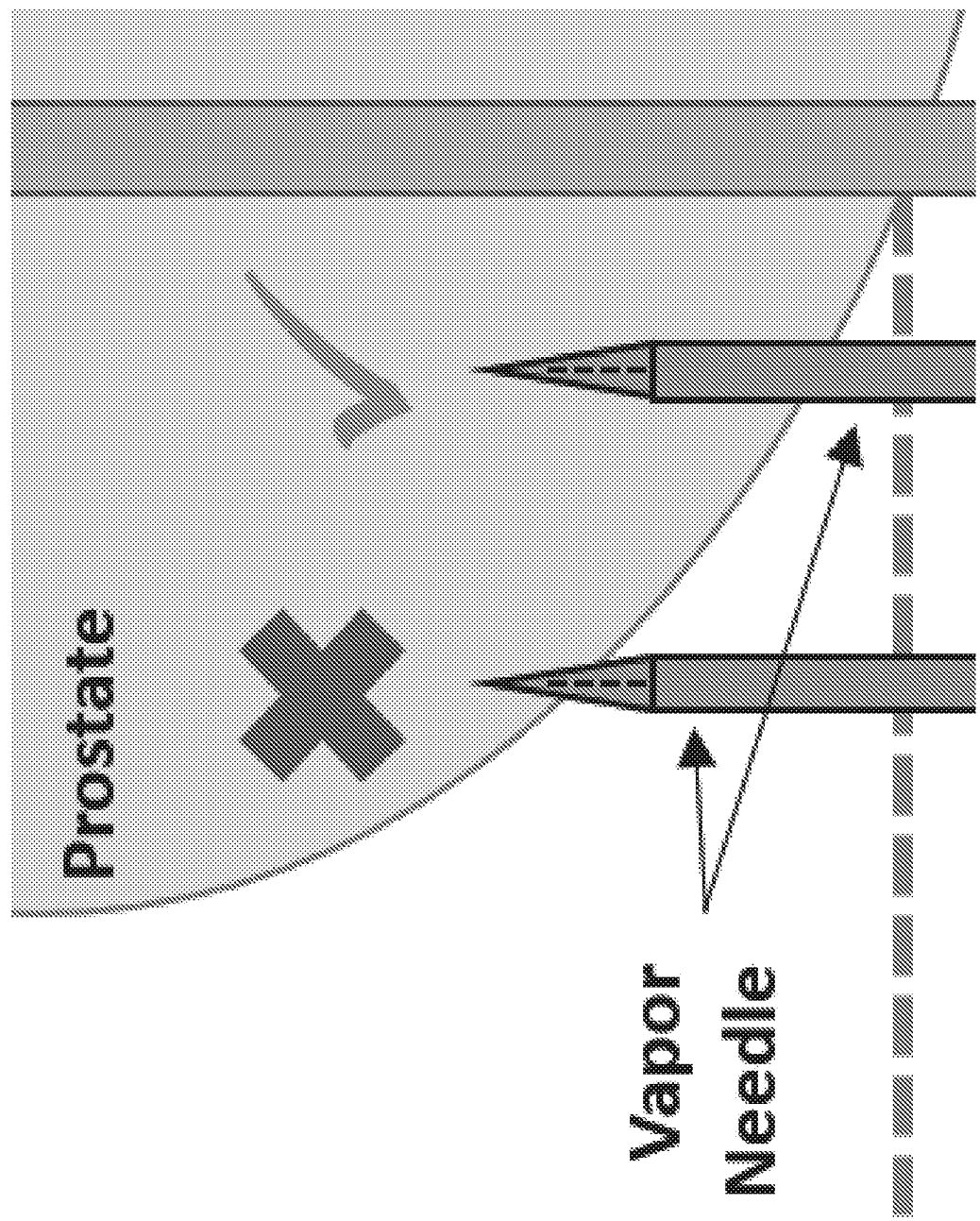
FIG. 5 shows an ambiguity in properly placing needles in the prostate with ultrasound imaging guidance.

Because the prostate is a 3D organ but the ultrasound data is ultimately rendered into a 2D image, it can be challenging for the physician to confirm that the vapor emitter holes are fully contained within the prostate. This is particularly true when pulling the needle back towards the perineum to treat apically. FIG. 5 demonstrates this concept visually. The vertical segment signifies the plane of the prostate that is being picked up by the ultrasound and viewed by the physician.

In this example, because the ultrasound is not measuring the exact plane in which the vapor needle lies, the user may incorrectly assume that the prostate extends further than it actually does in the axis of the vapor needle (this is represented by the dashed line). In the case of the vapor needle on the right, this is acceptable, because the emitter holes are still fully contained within the prostate. However, in the case of the vapor needle on the left, this visualization challenge would result in vapor being delivered external to the prostate capsule. As such, a secondary indication of the location of the needle tip within the prostate to supplement ultrasound visualization is desired.

Biocapacitance Operating Principles

The present invention incorporates electrodes into a vapor delivery needle tip. A high frequency current is passed between the electrodes and the resulting voltage between the electrodes and phase shift between the voltage and current are measured. These measurements depend upon the nature of the tissue surrounding the needle tip. Tissue may be electrically resistive and/or capacitive, depending upon its content. Specifically, the measurements distinguish prostate tissue from surrounding tissue, enabling an unambiguous determination that the vapor delivery needle is in the prostate before vapor is delivered.

Figure 6:
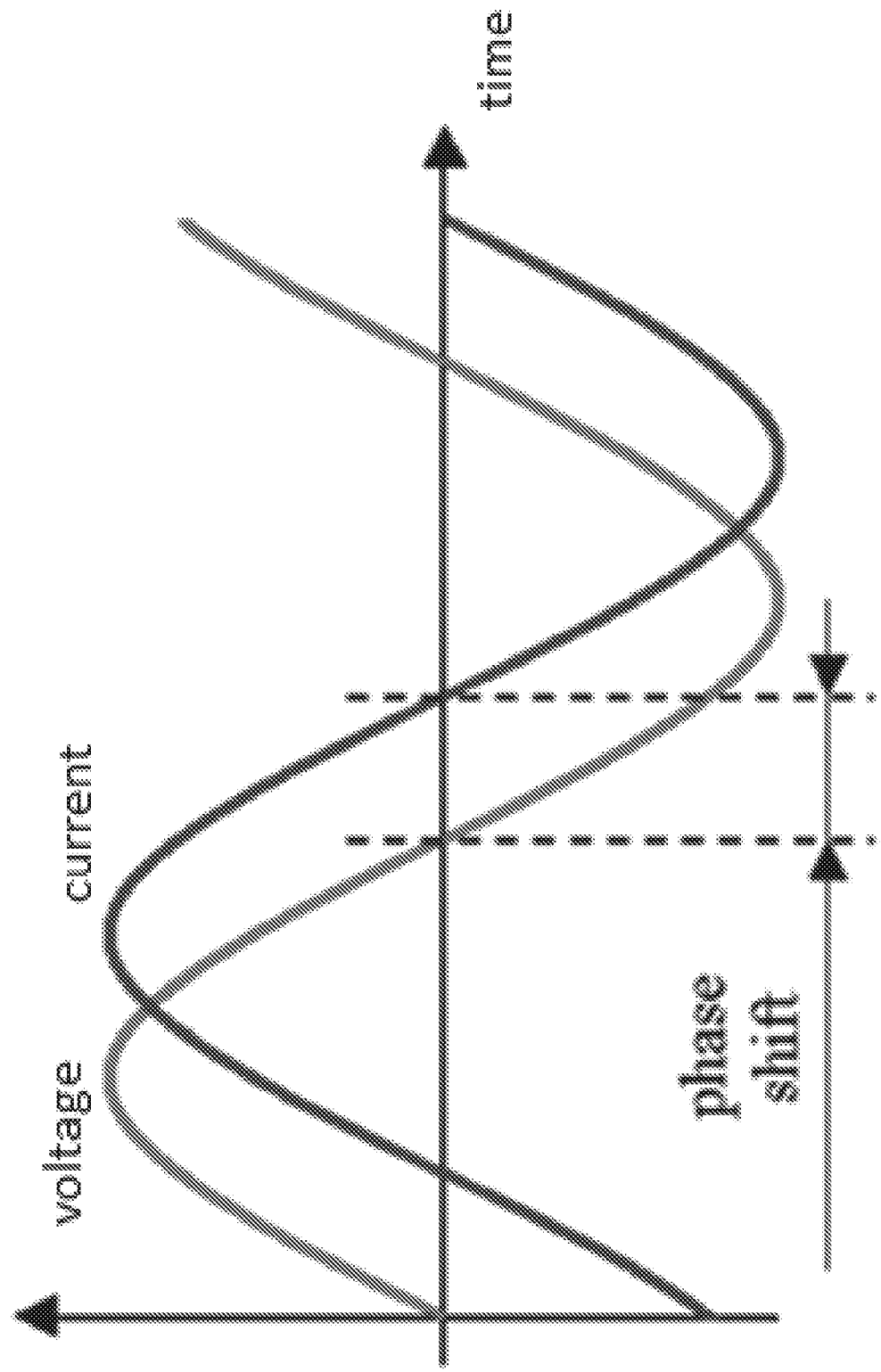
FIG. 6 shows the voltage and current and voltage signals between separated conductors.

In electronics, a capacitor is a circuit element that temporarily stores electrical energy in an electric field in the form of a charge. Capacitors come in a wide variety of shapes, sizes, and types that all share the common form of two electrical conductors separated by an insulating dielectric material. The dielectric material magnifies the capacitance by separating and storing charge. At a high level, the magnitude of the capacitance for a given capacitor is determined by the product of the surface area of the conductors and the dielectric constant of the material between them, divided by the separation between the conductors. For a given dielectric material, a capacitor consisting of large conductors that are very close together will have greater capacitance than one consisting of small conductors that are far apart. In an alternating current circuit, capacitance has the effect of causing the voltage signal to lag behind the current signal. The extent to which the voltage lags the current is measured in degrees between −90° and 90° and is commonly referred to as the "phase shift." FIG. 6 shows the current signal and voltage signal.

Similarly, the structure of human cells is such that they can be thought of as capacitive elements. The cell membrane is made up of a dielectric lipid bilayer that separates the conductive intracellular fluid from the conductive extracellular fluid, which together constitute the necessary elements to form a capacitor: two electrical conductors separated by a dielectric material. In living cellular tissue, ion pumps act within the cell membranes to actively transport charge across the membrane to maintain an electrical potential across the living cell membrane that is essential for life. Charge separation across the membranes is thereby retained and helps provide the living tissue capacitance. In general, tissue may have resistance in addition to capacitance, and electrodes separated by tissue constitute a "leaky capacitor", having both resistance and capacitance. Tissue that does not contain living cells is generally more resistive than capacitive. In theory, one could use the measurement of the capacitance of a segment of biological tissue as an indicator of the type of cells that make up that tissue. This can be thought of as measuring the biological capacitance, or bio-capacitance, of the tissue. In the present disclosure, a bio-capacitance measurement determines when the tip of the vapor needle is within the prostate vs. outside of the prostate and notifies the physician accordingly.

The prostate itself contains primarily stromal (smooth muscle) and glandular tissue cells, which due to their size and structure are generally characterized by medium impedance and medium-to-high capacitance. The areas immediately surrounding the prostate, on the other hand, typically contain fluid—which includes electrolytes, amino acids, and fatty acids and is therefore low in terms of both impedance and capacitance.

Also surrounding the prostate are various fascia, which are fibrous sheaths of tissue made up of collagen formed by long-chain proteins. Due to its long, thin structure, this collagen has lower impedance and capacitance than the stromal and glandular tissue within the prostate, but higher impedance and capacitance than the fluid outside of the prostate, which lacks cohesive structure. The prostate capsule is a fascia as well. Further away from the prostate but still in the path of the needle lie skin and fat cells, which due to their structure have impedance and capacitance more similar to the stromal and glandular tissue within the prostate. Table I shows an approximate map of the theoretical impedance and capacitance of the tissue on the path a therapy needle takes from the perineum to the prostate.

TABLE I

Impedance and Capacitance by Location

| Measurement | Skin | Fat | Fascia | Fluid | Capsule | Prostate |
| --- | --- | --- | --- | --- | --- | --- |
| Impedance | Medium | High | Low | Very Low | Low | Medium |
| Capacitance | High | High | Low | Very Low | Low | High |

Biocapacitance System Detailed Description

FIG. 4C shows the tip 123 of a vapor delivery needle having 3 columns of 4 emitter holes that expel vapor during therapy. The tip itself is the first electrode for the bio-capacitance measurement. The second electrode is a ring electrode 180 that is electrically separated from the needle tip by a section of PTFE insulation 182. An insulated nickel wire is welded to this electrode and runs down the length of the needle. Internal to the vapor needle assembly, the two electrodes are soldered to a 6" segment of MMCV coaxial cable, which terminates in a male MMCX connector. The vapor needle connects to a vector voltmeter circuit inside the system generator via an 8' MMCX coaxial extension cable and an MMXC to N-type adapter. The circuit supplies alternating current with a frequency that may be varied from one to 100 MHz, and performs an initial frequency sweep to determine an operating frequency that optimizes the impedance and phase contrast between tissues within and outside the prostate. Impedance amplitude and phase are outputs of the vector voltmeter circuit that are analyzed in the system computer.

The user workflow begins by manually identifying tissue that lies outside and inside the prostate. In this step, the system sweeps frequency and searches for a frequency between 1 and 100 MHz that shows the greatest separation in impedance magnitude and phase between tissue inside and outside the prostate. Calculation of phase and amplitude scores are performed using the formulas in Table 2 below. The scores are from zero (needle outside prostate) to 100 (needle inside prostate), and are based upon the initial calibration of phase and magnitude for tissues inside and outside the prostate. Once the calibration step is complete, the system identifies in real time the tissue type at the tip of the needle in the large, which can be displayed on the display to the user. Vapor can only be delivered to tissue when it is determined that both impedance measurements indicate that both the tip and ring electrodes are inside the prostate. The user is advised of conditions where only one electrode is inside the prostate, and when both electrodes are outside the prostate.

TABLE 2

Biocapacitance Score Calculation

Req BSRS1020 Raw Biocap Phase Score Calculation. ACPS228
A [Raw Biocap Phase Score] shall be calculated as the area under the phase angle vs. frequency curve using the trapezoidal numeric integration method.
Req BSRS1021 Raw Biocap Magnitude Score Calculation. ACPS228
A [Raw Biocap Mag Score] shall be calculated as the area under the magnitude vs. frequency curve using the trapezoidal numeric integration method.
Req BSRS1030 Biocap Phase Score Calculation. ACPS228
A [Biocap Phase Score] shall be calculated using the saved internal and external biocap data from the selected needle per the following formula:
[Biocap Phase Score] =

$$[\text{Raw } Biocap \text{ Phase Score}] - \frac{[\text{Raw External } Biocap \text{ Phase Score}]}{2 * ([\text{Raw Internal } Biocap \text{ Phase Score}] - [\text{Raw External } Biocap \text{ Phase Score}])} \times 100$$

Req BSRS1041 Biocap Magnitude Score Calculation. ACPS228
A [Biocap Mag Score] shall be calculated using the saved internal and external biocap data from the selected needle per the following formula:
[Biocap Mag Score] =

$$[\text{Raw } Biocap \text{ Mag Score}] - \frac{[\text{Raw External } Biocap \text{ Mag Score}]}{2 * ([\text{Raw Internal } Biocap \text{ Mag Score}] - [\text{Raw External } Biocap \text{ Mag Score}])} \times 100$$

Req BSRS1042BSRS1042 Biocap Composite Score Calculation. ACPS228
A [Biocap Composite Score] shall be calculated using the [Biocap Phase Score] and [Biocap Magnitude Score] per the following formula, where the
Weight is the value of the Biocap Score Weighting scale on the Settings tab divided by 100:
[Biocap Composite Score] =
  ([Biocap Phase Score] * Weight + [Biocap Mag Score] *
  (1 − Weight)) × 100

The Weight is adjustable via a sliding scale on the user interface to allow the user to bias the composite score to focus more or less on phase vs. magnitude.

Urethra Cooling System

The urethral cooling catheter 110 shown in FIG. 1B is inserted through the urethra until the tip is in the bladder. The fixation balloon 113 is inflated with saline via a 10 cc syringe to anchor the tip. The catheter is pulled back to engage the fixation balloon 113 against the inside wall of the bladder. These steps are similar to insertion of a Foley catheter.

Figure 7:
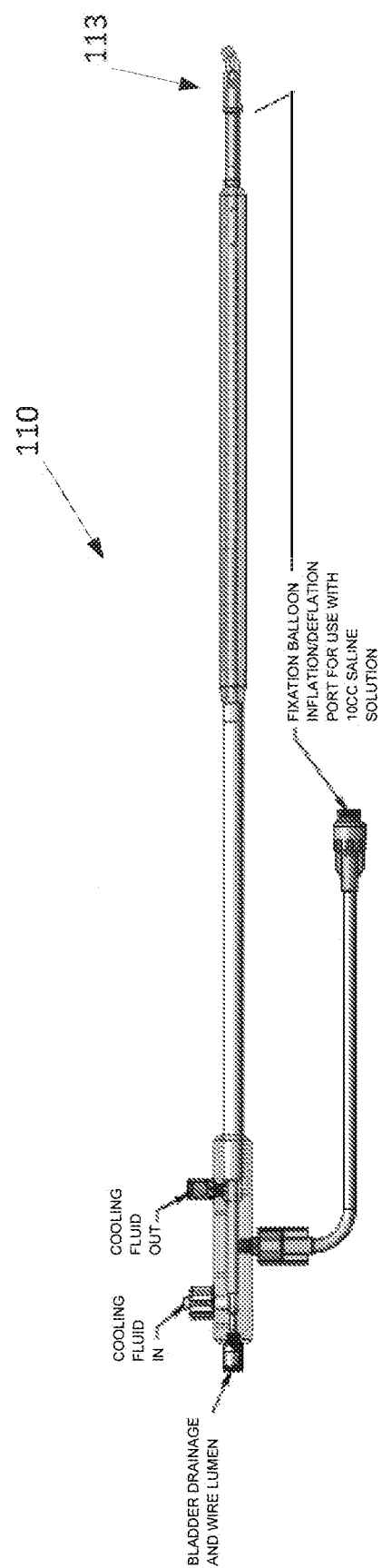
FIG. 7 illustrates a urethral cooling catheter.

The cooling catheter 110 is shown in more detail in FIG. 7. A central lumen allows insertion of the catheter over a guide wire, and provides a lumen for bladder drainage. Chilled water is circulated through a catheter lumen into the distal end of the fixation balloon 113, flowing down the length of the cooling balloon and out through the outer lumen of the catheter. Heat generated by vapor therapy inside the prostate is conducted away from the urethra wall by the circulating chilled water.

The chiller water circulates through the chilled saline 109 shown in FIG. 1A and back to the catheter. The chilled saline is inserted into a Peltier effect chiller located inside the auxiliary controller console. A peristaltic pump circulates the chilled water at a rate of about 150 ml/min. A preferred range of chilled water flow rate is 125 ml/min to 175 ml/min. Water exits the chilled saline 109 at a temperature of about 5° C. An ideal temperature of water exiting the chiller is 1° C., and temperatures below 10° C. are preferred.

Methods for Using the Trans-Perineal Prostate Cancer Therapy System

Vapor therapy treatments may be pre-planned based upon pre-treatment MRI and/or ultrasound images, and biopsies of the prostate. A treatment plan may comprise placement of vapor delivery needles in zones of the prostate that have been diagnosed as cancerous. Individual needles may apply multiple therapy shots to a given zone. One rule of thumb is that vapor treated tissue is less transparent to ultrasound than untreated tissue, therefore tissue furthest from the ultrasound transducer is treated first to insure optimal visualization on subsequent therapy shots.

One unique feature of vapor is that it does not cross prostate zone boundaries. This provides a unique protection for tissues outside the zone being treated. However, heat may be conducted across tissue boundary layers, a time dependent process. Ablation temperatures may be reached in adjacent zone tissue or in tissue outside the prostate capsule if vapor therapy is applied for a time that is long enough for sufficient heat to be conducted across the separating boundary layers. For this reason, vapor therapy is applied for a maximum of 15 seconds or a maximum of 10 seconds depending upon the size of the treatment zone.

Vapor has the unique property of being echoic to ultrasound energy, and the advance of vapor during therapy is readily visualized. Vapor reaches most of the tissue to be treated in the first second of therapy, but can often advance further over time. The operator may terminate therapy at any time he determines that a sufficient volume of tissue has been treated. Treatment times may be in the range of 5 to 10 seconds or in the range of 5 to 15 seconds. Treatment can be stopped at any time if the operator perceives a problem. Multiple therapy shots are applied until the desired tissue volume has been treated, which may generally comprise an entire prostate zone, or a portion of a zone.

Figure 8:
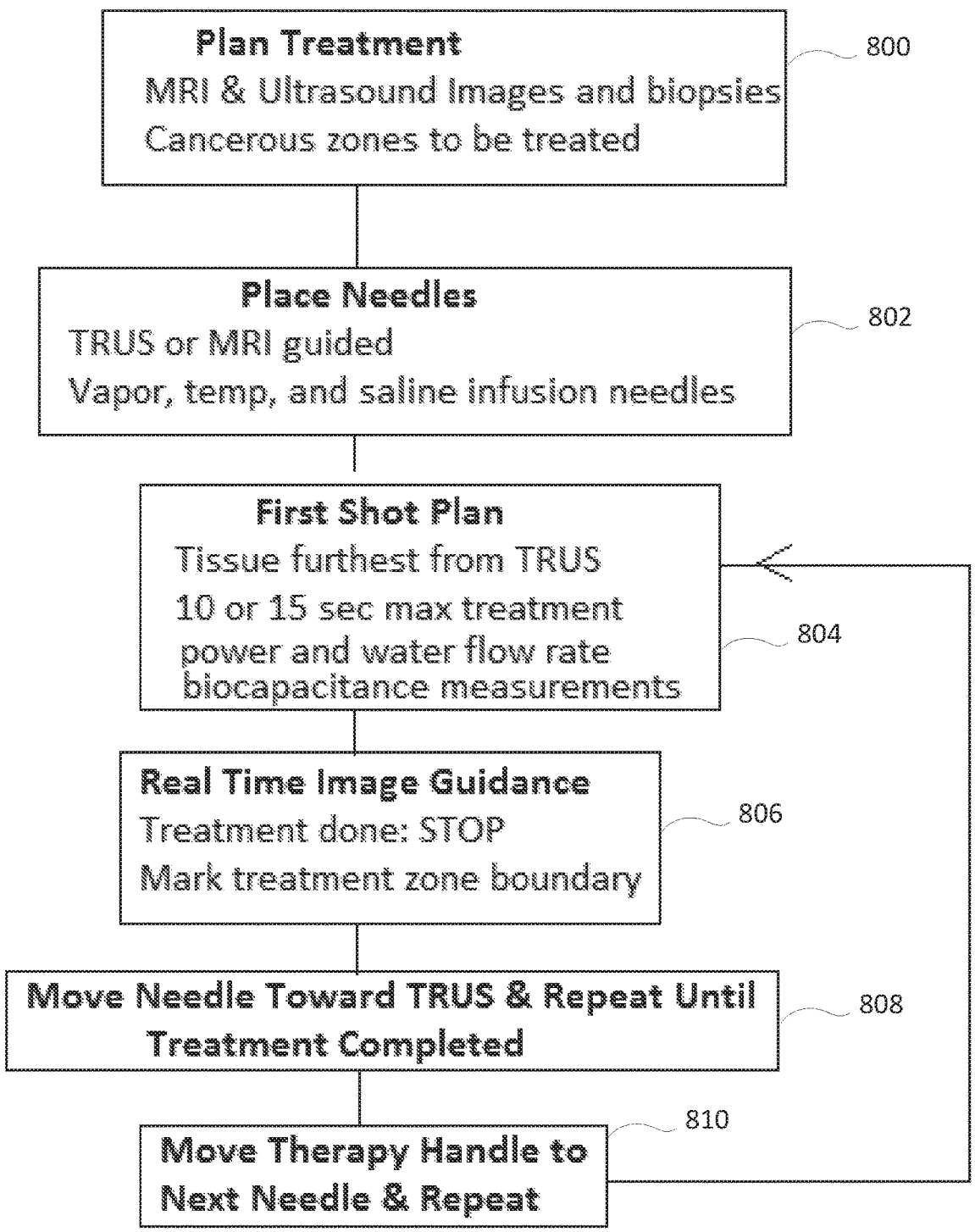
FIG. 8 provides a method of treating prostate cancer with a trans-perineal vapor delivery system.

FIG. 8 shows a block diagram of a method for treating prostate cancer with vapor therapy. The method begins with treatment planning at step 800, based upon pre-treatment images and biopsies, and may include TRUS images taken just prior to treatment. The plan includes identifying prostate zones, including for example peripheral zones and transition zones, that are cancerous and need to be treated.

At step 802, needles are next placed based upon the treatment plan. The needles may be placed under ultrasound or MRI guidance. With MRI guidance all instruments used in the procedure must be non-magnetic, and care must be taken to provide electromagnetic compatibility between RF therapy and MR images. Vapor, saline infusion, and thermocouple needles are placed in this step.

Next, the first vapor therapy shot is planned, including positioning the needle in untreated tissue that is farthest from the TRUS transducer for optimum imaging. A maximum treatment time is normally selected as 10 or 15 seconds based upon the size of the tissue region expected to be treated. Therapy RF power and sterile water flow rate are selected to expand vapor throughout the tissues expected to be treated on the current shot. The bio-capacitance method of FIG. 7 is employed to insure that the vapor needles are in prostate tissue before therapy is delivered.

Therapy is delivered at step 804, and the treatment is observed on the TRUS image at step 806 as vapor expands through the treatment region, or on an MRI thermal image as the temperature front advances. Therapy may be stopped at any time by releasing the therapy button on the hand piece. Otherwise treatment proceeds to the maximum time selected. The extent of treated tissue is noted, either by observations of vapor advancement on the TRUS image, or by the margins of the ablation zone on an MRI thermal image. With this information, the next region of therapy may be selected at step 808 and the vapor needle is moved, again under imaging and bio-capacitance guidance. This step is repeated until the entire prostate zone is treated. The delivery device handle is moved at step 810 to the next treatment needle and the process is repeated until all planned prostate zones have been treated.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A medical device comprising:
    a needle;
    a first electrode disposed at a distal tip of the needle, wherein the first electrode is configured to measure a first electrical impedance of a first tissue contacting the first electrode, and wherein the distal tip of the needle is the first electrode;
    a second electrode disposed on the needle, proximally of the first electrode, wherein the second electrode is configured to measure a second electrical impedance of a second tissue contacting the second electrode; and
    an electrically insulative material disposed between the first electrode and the second electrode; and
    an electronic controller configured to use the first electrical impedance and the second electrical impedance in order to determine whether the first electrode and the second electrode are disposed within a prostate.

2. The medical device of claim 1, wherein the first electrode is configured to measure a first phase shift of the first tissue.

3. The medical device of claim 2, wherein the second electrode is configured to measure a second phase shift of the second tissue.

4. The medical device of claim 3, wherein the controller is configured to use the first phase shift and the second phase shift in order to determine whether the first electrode and the second electrode are disposed within the prostate.

5. The medical device of claim 1, wherein the needle includes at least one hole configured to delivery vapor to the prostate.

6. The medical device of claim 1, further comprising circuitry electrically connected to the first electrode and the second electrode, wherein the circuitry is configured to provide a variable frequency.

7. The medical device of claim 1, wherein the needle includes a conductive inner tube and an insulative tube between the second electrode and the conductive inner tube.

8. A medical device comprising:
    a needle terminating in a distal tip, wherein the distal tip is a first electrode configured to measure a first electrical impedance of a first tissue contacting the first electrode, the needle including:
        a second, ring electrode, proximal of the first electrode, configured to measure a second electrical impedance of a second tissue contacting the second electrode; and
        an electrically insulative material disposed between the first electrode and the second electrode; and
    an electronic controller configured to use the first electrical impedance and the second electrical impedance in order to determine whether the first electrode and the second electrode are disposed within a prostate.

9. The medical device of claim 8, wherein the first electrode is configured to measure a first phase shift of the first tissue.

10. The medical device of claim 9, wherein the second electrode is configured to measure a second phase shift of the second tissue.

11. The medical device of claim 10, wherein the controller is configured to use the first phase shift and the second phase shift in order to determine whether the first electrode and the second electrode are disposed within the prostate.

12. The medical device of claim 8, wherein the needle includes at least one hole configured to deliver vapor to the prostate.

13. The medical device of claim 8, further comprising circuitry electrically connected to the first electrode and the second electrode, wherein the circuitry is configured to provide a variable frequency.

14. The medical device of claim 8, wherein the needle includes a conductive inner tube and an insulative tube between the second electrode and the conductive inner tube.

15. A medical device comprising:
    a needle terminating in a distal tip, wherein the distal tip is a first electrode configured to measure a first electrical impedance and a first phase shift of a first tissue contacting the first electrode, the needle including:
        a second electrode, proximal of the first electrode, configured to measure a second electrical impedance and a second phase shift of a second tissue contacting the second electrode; and
        an electrically insulative material disposed between the first electrode and the second electrode; and
    an electronic controller configured to use the first electrical impedance, the first phase shift, the second electrical impedance, and the second phase shift, in order to determine whether the first electrode and the second electrode are disposed within a prostate.

16. The medical device of claim 15, wherein the needle includes at least one hole configured to deliver vapor to a prostate.

17. The medical device of claim 15, further comprising circuitry electrically connected to the first electrode and the second electrode, wherein the circuitry is configured to provide a variable frequency.

* * * * *